(12) United States Patent
Alahmadi et al.

(10) Patent No.: US 11,834,394 B2
(45) Date of Patent: Dec. 5, 2023

(54) METHANOL PRODUCTION PROCESS WITH INCREASED ENERGY EFFICIENCY

(71) Applicant: ENI S.P.A., Rome (IT)

(72) Inventors: Faisal Alahmadi, Thuwal (SA); Marwan Alamro, Thuwal (SA); Aspi Kolah, Thuwal (SA)

(73) Assignee: ENI S.P.A., Rome (IT)

( * ) Notice: Subject to any disclaimer, the term of this patent is extended or adjusted under 35 U.S.C. 154(b) by 196 days.

(21) Appl. No.: 17/428,533

(22) PCT Filed: Feb. 6, 2020

(86) PCT No.: PCT/IB2020/050961
§ 371 (c)(1),
(2) Date: Aug. 4, 2021

(87) PCT Pub. No.: WO2020/161667
PCT Pub. Date: Aug. 13, 2020

(65) Prior Publication Data
US 2022/0194884 A1 Jun. 23, 2022

Related U.S. Application Data

(60) Provisional application No. 62/801,998, filed on Feb. 6, 2019.

(51) Int. Cl.
*C07C 29/151* (2006.01)
*C01B 3/38* (2006.01)

(52) U.S. Cl.
CPC .......... *C07C 29/1518* (2013.01); *C01B 3/386* (2013.01)

(58) Field of Classification Search
CPC ..... C07C 29/1518; C07C 31/04; C01B 3/386; C01B 2203/0233; C01B 3/382;
(Continued)

(56) References Cited

U.S. PATENT DOCUMENTS

2008/0069766 A1 3/2008 Rojey et al.
2015/0087865 A1 3/2015 Iaquaniello et al.

FOREIGN PATENT DOCUMENTS

DE 3521304 A1 12/1986
EP 2116295 A1 11/2009

OTHER PUBLICATIONS

International Search Report dated Apr. 20, 2020 re: Application No. PCT/IB2020/050961, pp. 1-4, citing: US 2008/069766 A1, US 2015/087865 A1, EP 2 116 295 A1 and DE 35 21 304 A1.

(Continued)

*Primary Examiner* — Jafar F Parsa
(74) *Attorney, Agent, or Firm* — CANTOR COLBURN LLP

(57) ABSTRACT

A system having a catalytic partial oxidation (CPO) reactor operable to produce a CPO reactor effluent characterized by a hydrogen to carbon monoxide ($H_2$/CO) molar ratio and an M ratio ($H_2$—$CO_2$)/(CO+$CO_2$); a steam methane reforming (SMR) reactor operable to produce an SMR reactor effluent characterized by a $H_2$/CO molar ratio greater than that of the CPO reactor effluent, and an M ratio greater than that of the CPO reactor effluent. The system includes a flow line(s) configured to combine at least a portion of the CPO reactor effluent with at least a portion of the SMR reactor effluent to provide a combined syngas stream upstream or downstream of a heat exchanger operable to transfer heat from at least a portion of the CPO reactor effluent, at least a portion of the SMR reactor effluent, or the combined syngas stream to the first portion and/or the second portion of hydrocarbons.

20 Claims, 1 Drawing Sheet

(58) Field of Classification Search
CPC .... C01B 2203/0205; C01B 2203/0261; C01B 2203/061; C01B 2203/0894; C01B 2203/1241; Y02P 20/10
See application file for complete search history.

(56) References Cited

OTHER PUBLICATIONS

Written Opinion dated Apr. 20, 2020 re: Application No. PCt/IB2020/050961, pp. 1-4, citing: US 2008/069766 A1, US 2015/087865 A1, EP 2 116 295 A1 and DE 35 21 304 A1.

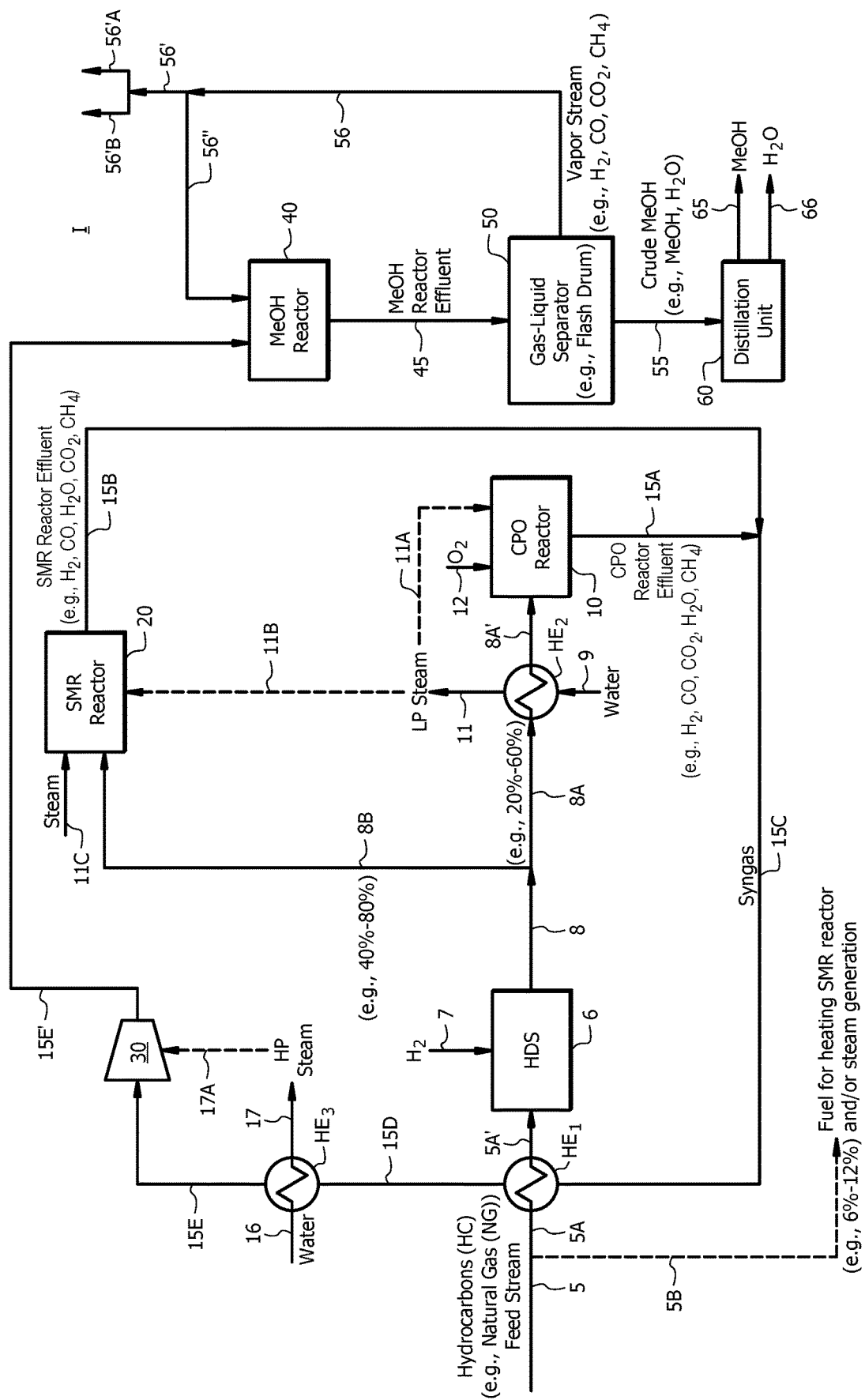

METHANOL PRODUCTION PROCESS WITH INCREASED ENERGY EFFICIENCY

TECHNICAL FIELD

The present disclosure relates to systems and processes for producing synthesis gas via catalytic partial oxidation (CPO), and the production of methanol therefrom; more specifically, the present disclosure relates to systems and processes for producing methanol that utilize steam methane reforming (SMR) and catalytic partial oxidation (CPO) to provide synthesis gas for methanol production; still more specifically, the present disclosure relates to systems and processes of producing methanol that provide a synthesis gas feed having a desired composition within the methanol synthesis loop via a combination of CPO and SMR, without the use of additional hydrogen enrichment, for example via WGS, and/or carbon dioxide ($CO_2$) removal.

BACKGROUND

Synthesis gas (syngas) is a mixture comprising carbon monoxide (CO) and hydrogen ($H_2$), as well as small amounts of carbon dioxide ($CO_2$), water ($H_2O$), and unreacted methane ($CH_4$). Syngas is generally used as an intermediate in the production of methanol and ammonia, as well as an intermediate in creating synthetic petroleum to use as a lubricant or fuel.

Syngas is produced conventionally by steam reforming of natural gas (steam methane reforming or SMR), although other hydrocarbon sources can be used for syngas production, such as refinery off-gases, naphtha feedstocks, heavy hydrocarbons, coal, biomass, etc. SMR is an endothermic process and requires significant energy input to drive the reaction forward. Conventional endothermic technologies such as SMR produce syngas with a hydrogen content greater than the required content for methanol synthesis. Generally, SMR produces syngas with an M ratio ranging from 2.6 to 2.98, wherein the M ratio is a molar ratio defined as ($H_2$—$CO_2$)/(CO+$CO_2$).

In an autothermal reforming (ATR) process, a portion of the natural gas is burned as fuel to drive the conversion of natural gas to syngas resulting in relatively low hydrogen and high $CO_2$ concentrations. Conventional methanol production plants utilize a combined reforming (CR) technology that pairs SMR with autothermal reforming (ATR) to reduce the amount of hydrogen present in syngas. ATR produces a syngas with a hydrogen content lower than that required for methanol synthesis. Generally, ATR produces syngas with an M ratio ranging from 1.7 to 1.84. In the CR technology, the natural gas feed volumetric flowrate to the SMR and the ATR can be adjusted to achieve an overall syngas M ratio of 2.0 to 2.06. Further, CR syngas has a hydrogen content greater than that required for methanol synthesis. Furthermore, SMR is a highly endothermic process, and the endothermicity of the SMR technology requires burning fuel to drive the syngas synthesis. Consequently, the SMR technology reduces the energy efficiency of the methanol synthesis process.

Syngas can also be produced (non-commercially) by catalytic partial oxidation (CPO or CPOx) of natural gas. CPO processes employ partial oxidation of hydrocarbon feeds to syngas comprising CO and $H_2$. The CPO process is exothermic, thus eliminating the need for external heat supply. However, the composition of the produced syngas is not directly suitable for a variety of downstream syntheses (e.g., methanol synthesis) owing to a reduced hydrogen content. Thus, there is an ongoing need for the development of systems and processes that utilize CPO processes for the production of synthesis gas suitable for downstream chemical synthesis (e.g., methanol synthesis).

BRIEF DESCRIPTION OF THE DRAWINGS

For a detailed description of the preferred embodiments of the disclosed processes, reference will now be made to the accompanying drawing in which:

The FIGURE is a schematic of a system I for a synthesis gas and methanol synthesis process, according to embodiments of this disclosure.

DETAILED DESCRIPTION

Herein disclosed are a system and process for syngas production and optionally subsequent methanol synthesis therefrom using catalytic partial oxidation (CPO) of, for example, natural gas, in combination with SMR.

Conventional processes to produce syngas for methanol synthesis utilize standalone Steam Reforming (SMR) technology or combined reforming (CR) technology. Both of these conventional processes utilize endothermic steam reforming (SMR) to produce syngas with the required composition for methanol synthesis. The SMR reaction is a highly endothermic unit operation that is also high in capital expenses (CAPEX). Conventional best in class methanol plants utilize a combined reforming (CR) technology that consists of an SMR reactor and an Auto Thermal Reformer (ATR) to reduce the energy intensity of the syngas production, and thus of the overall methanol synthesis process. The CR process reduces the fuel consumption of the SMR unit by introducing an ATR to reform part of the natural gas feed. The natural gas feed (e.g., the volumetric flowrate) to the SMR and the ATR is adjusted to achieve an overall syngas composition (e.g., a syngas with an M value, as described further hereinbelow, of from about 2.0 to 2.06) produced by the CR technology.

The endothermicity of the SMR technology requires burning of a fuel to drive the reactions. Consequently, the SMR technology reduces the energy efficiency of a methanol synthesis process employing SMR to provide the synthesis gas feed to the methanol synthesis.

The herein disclosed system and process utilize a CPO process in conjunction with SMR to produce a hydrogen enriched syngas with the required composition for downstream methanol synthesis without the need for additional hydrogen enrichment, for example via water gas shift (WGS) and/or carbon dioxide ($CO_2$) removal. According to this disclosure, a catalytic partial oxidation reactor (CPO) can be installed in parallel to a steam methane reformer (SMR), with a process hydrocarbon feed divided with about 10 to about 70 wt % or from about 20 to about 60 wt % being directed to a CPO reactor and the balance (about 30 to about 90 wt % or about 40 to about 80 wt %) being directed to an SMR reactor. The herein disclosed methanol synthesis system and process are energy efficient and can be utilized, in embodiments, in a retrofit of an existing methanol production plant. By utilizing CPO, along with SMR and/or heat integration, the herein disclosed system and process allow for a reduced energy utilization with minimal capital expenditures.

In embodiments, the energy intensity of an existing methanol plant can be reduced according to this disclosure by retrofitting the existing plant. Alternatively, a new methanol plant having reduced energy intensity relative to a similar plant absent the CPO can be designed according to this disclosure. The energy intensity is minimized according to this disclosure by integrating catalytic partial oxidation with SMR to produce similar or higher production rates of methanol with similar product quality. In embodiments, the energy intensity of a methanol synthesis plant (e.g., of a new or existing plant retrofitted as per this disclosure) is reduced from an indexed value of 90 to 100 MMBTU/ton of methanol produced to an indexed value of less than about 55 to 85 MMBTU/ton of methanol produced, which can represent a reduction of more than about 15 to 45%. In embodiments, the energy intensity of methanol production is reduced via the system and process of this disclosure by at least 5, 10, 15, 20, 25, 30, 35, 40, or 45% relative to conventional methanol production via SMR without CPO. In embodiments, the energy intensity of a methanol synthesis plant (e.g., of a new or existing plant retrofitted as per this disclosure) is reduced to an indexed value of less than or equal to about 90, 85, 80, 75, 70, 65, 60, or 55 MMBTU/ton of methanol produced via the system and process of this disclosure.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or process steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having greater than or equal to x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

As utilized herein, the 'methanol synthesis loop' or 'methanol loop' refers to the methanol synthesis section of a plant, comprising the methanol synthesis reactor(s).

As utilized herein, the M ratio is a molar ratio defined as $(H_2-CO_2)/(CO+CO_2)$.

Referring to The FIGURE, a syngas and methanol production system I is disclosed. The syngas and methanol production system I generally comprises a catalytic partial oxidation (CPO or CPOx) reactor 10; a steam methane reforming (SMR) reactor 20; a compressor 30; a methanol reactor 40; a gas-liquid separator 50; and a distillation unit 60. In embodiments, the syngas and methanol synthesis system I can further comprise a desulfurization unit 6, and one or more heat exchangers, such as first heat exchanger HE1, second heat exchanger HE2, and third heat exchanger HE3. As will be appreciated by one of skill in the art, and with the help of this disclosure, syngas and methanol production system components shown in The FIGURE can be in fluid communication with each other (as represented by the connecting lines indicating a direction of fluid flow) through any suitable conduits (e.g., pipes, streams, etc.).

In embodiments, a process as disclosed herein can comprise a step of (a) feeding a catalytic partial oxidation (CPO) reactant mixture to a CPO reactor 10; wherein the CPO reactant mixture comprises oxygen, a first portion 8A of hydrocarbons, and optionally steam; wherein at least a portion of the CPO reactant mixture reacts, via a CPO reaction, in the CPO reactor 10 to produce a CPO reactor effluent 15A; wherein the CPO reactor 10 comprises a CPO catalyst; wherein the CPO reactor effluent 15A comprises hydrogen ($H_2$), carbon monoxide (CO), carbon dioxide ($CO_2$), water, and unreacted hydrocarbons, wherein the CPO reactor effluent 15A is characterized by a hydrogen to carbon monoxide ($H_2$/CO) molar ratio of the CPO reactor effluent 15A, and wherein the CPO reactor effluent 15A is characterized by an M ratio of the CPO reactor effluent 15A, wherein the M ratio is a molar ratio defined as $(H_2-CO_2)/(CO+CO_2)$. As described further hereinbelow, the CPO reactant mixture can comprise oxygen in line 12 and/or steam in line 11A in combination with a first hydrocarbon portion 8A.

The process further comprises (b) feeding a steam methane reforming (SMR) reactant mixture to an SMR reactor 20, wherein the SMR reactant mixture comprises steam and a second portion 8B of hydrocarbons; wherein at least a portion of the SMR reactant mixture reacts, via an SMR reaction, in the SMR reactor 20 to produce an SMR reactor effluent 15B; wherein the SMR reactor effluent 15B comprises hydrogen ($H_2$), carbon monoxide (CO), carbon dioxide ($CO_2$), water, and unreacted hydrocarbons; wherein the SMR reactor effluent 15B is characterized by a $H_2/CO$ molar ratio of the SMR reactor effluent 15B that is greater than the $H_2/CO$ molar ratio of the CPO reactor effluent 15A; and wherein the SMR reactor effluent 15B is characterized by an M ratio of the SMR reactor effluent 15B that is greater than the M ratio of the CPO reactor effluent 15A. As described further hereinbelow, the SMR reactant mixture can comprise steam in line 11A and/or 11C in combination with the second hydrocarbon portion 8B.

Generally, the CPO reaction is based on partial combustion of fuels, such as various hydrocarbons, and in the case of methane, CPO can be represented by Equation (1):

$$CH_4 + \tfrac{1}{2}O_2 \rightarrow CO + 2H_2 \qquad (1)$$

Without wishing to be limited by theory, side reactions can take place along with the CPO reaction depicted in Equation (1); and such side reactions can produce carbon dioxide ($CO_2$) and water ($H_2O$), for example via hydrocarbon combustion, which is an exothermic reaction. As will be appreciated by one of skill in the art, and with the help of this disclosure, and without wishing to be limited by theory, the CPO reaction as represented by Equation (1) can yield a syngas with a hydrogen to carbon monoxide ($H_2/CO$) molar ratio having the theoretical stoichiometric limit of 2.0. Without wishing to be limited by theory, the theoretical stoichiometric limit of 2.0 for the $H_2/CO$ molar ratio means that the CPO reaction as represented by Equation (1) yields 2 moles of $H_2$ for every 1 mole of CO, i.e., $H_2/CO$ molar ratio of (2 moles $H_2$/1 mole CO)=2. As will be appreciated by one of skill in the art, and with the help of this disclosure, the theoretical stoichiometric limit of 2.0 for the $H_2/CO$ molar ratio in a CPO reaction cannot be achieved practically because reactants (e.g., hydrocarbons, oxygen) as well as products (e.g., $H_2$, CO) undergo side reactions at the conditions used for the CPO reaction. As will be appreciated by one of skill in the art, and with the help of this disclosure, and without wishing to be limited by theory, in the presence of oxygen, CO and $H_2$ can be oxidized to $CO_2$ and $H_2O$, respectively. The relative amounts (e.g., composition) of CO, $H_2$, $CO_2$ and $H_2O$ can be further altered by the equilibrium of the water-gas shift (WGS) reaction, which will be discussed in more detail later herein. The side reactions that can take place in the CPO reactor 10 can have a direct impact on the M ratio of the produced syngas (e.g., the syngas in CPO reactor effluent 15A), wherein the M ratio is a molar ratio defined as ($H_2$—$CO_2$)/(CO+$CO_2$). In the absence of any side reaction (theoretically), the CPO reaction as represented by Equation (1) results in a syngas with an M ratio of 2.0. However, the presence of side reactions (practically) reduces $H_2$ and increases $CO_2$, thereby resulting in a syngas in the CPO reactor effluent 15A with an M ratio below 2.0.

Further, without wishing to be limited by theory, the CPO reaction as depicted in Equation (1) is an exothermic heterogeneous catalytic reaction (i.e., a mildly exothermic reaction) and it occurs in a single reactor unit, such as the CPO reactor 10 (as opposed to more than one reactor unit as is the case in conventional processes for syngas production, such as steam methane reforming (SMR)—autothermal reforming (ATR) combinations). While it is possible to conduct partial oxidation of hydrocarbons as a homogeneous reaction, in the absence of a catalyst, homogeneous partial oxidation of hydrocarbons process entails excessive temperatures, long residence times, as well as excessive coke formation, which strongly reduce the controllability of the partial oxidation reaction, and may not produce syngas of the desired quality in a single reactor unit.

Furthermore, without wishing to be limited by theory, the CPO reaction is fairly resistant to chemical poisoning, and as such it allows for the use of a wide variety of hydrocarbon feedstocks, including some sulfur containing hydrocarbon feedstocks; which, in some cases, can enhance catalyst life-time and productivity. By contrast, conventional ATR processes have more restrictive feed requirements, for example in terms of content of impurities in the feed (e.g., feed to ATR is desulfurized), as well as hydrocarbon composition (e.g., ATR primarily uses a $CH_4$-rich feed).

Steam can react with methane, for example as represented by Equation (2):

$$CH_4 + H_2O \rightleftharpoons CO + 3H_2 \qquad (2)$$

The SMR reactor effluent 15B can be produced by reacting, via an SMR reaction (e.g., a reaction represented by Equation (2)), an SMR reactant mixture comprising the second portion 8B of hydrocarbons and steam 11B and/or 11C in the SMR reactor 20 to produce the SMR reactor effluent 15B; wherein the SMR reactant mixture thus comprises methane and steam; and wherein the SMR reactor effluent 15B comprises hydrogen, carbon monoxide, carbon dioxide, water, and unreacted methane.

Generally, SMR describes the catalytic reaction of methane and steam to form carbon monoxide and hydrogen according to the reaction represented by Equation (2). Steam reforming catalysts utilized in SMR reactor 20 can comprise any suitable commercially available steam reforming catalyst; nickel (Ni) and/or rhodium (Rh) as active metal(s) on alumina; or combinations thereof. SMR employs fairly elevated S/C molar ratios when compared to the S/C molar ratios used in CPO. For example, SMR reactor 20 can be characterized by an S/C molar ratio in the SMR reactant mixture of greater than or equal to about 1.5:1, alternatively greater than or equal to about 2:1, alternatively greater than or equal to about 2.5:1, alternatively greater than or equal to about 2.7:1, alternatively greater than or equal to about 3.0:1, or in a range of from about 1.5:1 to 3.5:1, from about 1.5:1 to 3:1, or from about 1.5:1 to about 2.5:1. Further, the SMR reactor effluent 15B can be characterized by a $H_2/CO$ molar ratio of greater than or equal to about 2.5, alternatively greater than or equal to about 2.7, or alternatively greater than or equal to about 2.9. As will be appreciated by one of skill in the art, and with the help of this disclosure, and without wishing to be limited by theory, the SMR reaction as represented by Equation (2) can yield a syngas with a $H_2/CO$ molar ratio having the theoretical stoichiometric limit of 3.0 (i.e., SMR reaction as represented by Equation (2) yields 3 moles of $H_2$ for every 1 mole of CO). As will be appreciated by one of skill in the art, and with the help of this disclosure, the theoretical stoichiometric limit of 3.0 for the $H_2/CO$ molar ratio in an SMR reaction cannot be achieved because reactants undergo side reactions at the conditions used for the SMR reaction. The M ratio of the SMR reactor effluent 15B is greater than the M ratio of the CPO reactor effluent 15A.

In embodiments, the hydrocarbon feed 5 further comprise one or more sulfur-containing compounds, and at least a portion of the sulfur-containing compounds is removed from a process portion 5A of the hydrocarbon feed 5 prior to introducing the hydrocarbons to the CPO reactor 10 as a component of the CPO reactant mixture or the SMR reactor 20 as a component of the SMR reactant mixture. In such embodiments, the process portion 5A (optionally following heat exchange thereto from CPO reactor effluent 15A, SMR reactor effluent 15B, or a combined syngas stream comprising at least a portion of the CPO reactor effluent 15A and at least a portion of the SMR reactor effluent 15B to provide heat exchanged process portion 5A' of hydrocarbons, which is described further hereinbelow) of hydrocarbon feed 5 can be introduced into a desulfurization unit 6 for the removal of one or more sulfur-containing compounds therefrom. Any suitable desulfurization unit 6 known to those of skill in the art can be utilized. For example, in embodiments, desulfurization unit 6 comprises a hydrodesulfurization (HDS) unit 6, and hydrogen is introduced into the desulfurization unit 6 via hydrogen line 7. A desulfurized hydrocarbon stream 8 can be removed from desulfurization unit 6. The desulfurized hydrocarbon stream 8 can be separated into a first hydrocarbon portion 8A, which is introduced into CPO reactor 10 as a component of the CPO reactant mixture (optionally following heat exchange therefrom to provide heat exchanged desulfurized first hydrocarbon portion 8A', which is described further hereinbelow), and a second hydrocarbon portion 8B, which is introduced into SMR reactor 20 as a component of the SMR reactant mixture.

In embodiments, a weight ratio of the first portion 8A of hydrocarbons to the second portion 8B of hydrocarbons is from about 1:9 to about 9:1, from about 1:9 to about 8:1, or from about 2:9 to about 9:1. In embodiments, the first portion 8A of hydrocarbons comprises greater than or equal to about 10, 20, 30, 40, 50, or 60 wt % of the total hydrocarbons 8 (e.g., the total hydrocarbons being the sum of the first portion 8A and the second portion 8B of hydrocarbons). In embodiments, the second portion 8B of hydrocarbons comprises less than or equal to about 90, 80, 70, 60, 50, or 40 wt % of the total hydrocarbons 8 (e.g., the total hydrocarbons being the sum of the first portion 8A and the second portion 8B of hydrocarbons).

In embodiments, the hydrocarbons (e.g., in hydrocarbon feed 5) suitable for use in a CPO and SMR reaction as disclosed herein can include methane ($CH_4$), natural gas, natural gas liquids, liquefied petroleum gas (LPG), associated gas, well head gas, enriched gas, paraffins, shale gas, shale liquids, fluid catalytic cracking (FCC) off gas, refinery process gases, refinery off gases, stack gases, fuel gas from a fuel gas header, and the like, or combinations thereof. The hydrocarbons can include any suitable hydrocarbons source, and can contain $C_1$-$C_6$ hydrocarbons, as well some heavier hydrocarbons.

In embodiments, the CPO reactant mixture in CPO reactor 10 and the SMR reactant mixture in SMR reactor 20 can comprise hydrocarbons from hydrocarbon feed 5, which can comprise, consist essentially of, or consist of natural gas. A process portion 5A of the hydrocarbon feed 5 can be utilized as process gas (e.g., process natural gas PNG)), and directed toward CPO reactor 10 or SMR reactor 20, while a fuel portion 5B of the hydrocarbon feed 5 can be utilized as fuel gas (e.g., fuel natural gas (FNG)), and directed elsewhere throughout system I for use as a fuel (e.g., combusted for steam generation, such as for the production of high pressure (HP) steam to run a turbine, e.g. to run a turbine of a steam-driven compressor 30 and/or to generate heat for heating the SMR reactor 20). In embodiments, the hydrocarbons of the fuel portion 5B of hydrocarbon feed 5 utilized as fuel comprise from about 5 to about 20, from about 5 to about 15, from about 6 to about 12 wt %, or less than about 20, 19, 18, 17, 16, 15, 14, 13, 12, 11, 10, 9, 8, 7, 6, 5, 4, 3, 2, or 1 wt. % of the total hydrocarbons of hydrocarbon feed 5, based on the total weight of the total hydrocarbons in hydrocarbon feed 5, wherein the total hydrocarbons are given by the sum of the hydrocarbons introduced to the CPO reactor 10 or the SMR reactor 20 of the process via process portion 5A and the hydrocarbons directed as fuel via fuel portion 5B.

Generally, natural gas is composed primarily of methane, but can also contain ethane, propane and heavier hydrocarbons (e.g., iso-butane, n-butane, iso-pentane, n-pentane, hexanes, etc.), as well as very small quantities of nitrogen, oxygen, carbon dioxide, sulfur compounds, and/or water. The natural gas can be provided from a variety of sources including, but not limited to, gas fields, oil fields, coal fields, fracking of shale fields, biomass, landfill gas, and the like, or combinations thereof. In some embodiments, the CPO reactant mixture and the SMR reactant mixture can comprise $CH_4$ and $O_2$.

The natural gas can comprise any suitable amount of methane. In some embodiments, the natural gas can comprise biogas. For example, the natural gas can comprise from about 45 mol % to about 80 mol % methane, from about 20 mol % to about 55 mol % carbon dioxide, and less than about 15 mol % nitrogen.

In embodiments, natural gas (or the hydrocarbons stream 5) can comprise $CH_4$ in an amount of greater than or equal to about 45 mol %, alternatively greater than or equal to about 50 mol %, alternatively greater than or equal to about 55 mol %, alternatively greater than or equal to about 60 mol %, alternatively greater than or equal to about 65 mol %, alternatively greater than or equal to about 70 mol %, alternatively greater than or equal to about 75 mol %, alternatively greater than or equal to about 80 mol %, alternatively greater than or equal to about 82 mol %, alternatively greater than or equal to about 84 mol %, alternatively greater than or equal to about 86 mol %, alternatively greater than or equal to about 88 mol %, alternatively greater than or equal to about 90 mol %, alternatively greater than or equal to about 91 mol %, alternatively greater than or equal to about 92 mol %, alternatively greater than or equal to about 93 mol %, alternatively greater than or equal to about 94 mol %, alternatively greater than or equal to about 95 mol %, alternatively greater than or equal to about 96 mol %, alternatively greater than or equal to about 97 mol %, alternatively greater than or equal to about 98 mol %, or alternatively greater than or equal to about 99 mol %.

In some embodiments, the hydrocarbon feed 5 suitable for use in a CPO and SMR reaction as disclosed herein can comprise $C_1$-$C_6$ hydrocarbons, nitrogen (e.g., from about 0.1 mol % to about 15 mol %, alternatively from about 0.5 mol % to about 11 mol %, alternatively from about 1 mol % to about 7.5 mol %, or alternatively from about 1.3 mol % to about 5.5 mol %), and carbon dioxide (e.g., from about 0.1 mol % to about 2 mol %, alternatively from about 0.2 mol % to about 1 mol %, or alternatively from about 0.3 mol % to about 0.6 mol %). For example, the hydrocarbons suitable for use in a CPO reaction as disclosed herein can comprise $C_1$ hydrocarbon (about 89 mol % to about 92 mol %); $C_2$ hydrocarbons (about 2.5 mol % to about 4 mol %); $C_3$ hydrocarbons (about 0.5 mol % to about 1.4 mol %); $C_4$ hydrocarbons (about 0.5 mol % to about 0.2 mol %); $C_5$ hydrocarbons (about 0.06 mol %); and $C_6$ hydrocarbons (about 0.02 mol %); and optionally nitrogen (about 0.1 mol % to about 15 mol %), carbon dioxide (about 0.1 mol % to about 2 mol %), or both nitrogen (about 0.1 mol % to about 15 mol %) and carbon dioxide (about 0.1 mol % to about 2 mol %). Accordingly, the CPO reactant mixture and the SMR reactant mixture can comprise such hydrocarbons, which can be introduced into CPO reactor 10 and SMR reactor 20 via process portion 5A of hydrocarbon feed 5, and first portion 8A or second portion 8B of hydrocarbons, respectively, or separately.

The oxygen used in the CPO reactant mixture 10 can comprise 100% oxygen (substantially pure $O_2$), oxygen gas (which may be obtained via a membrane separation process), technical oxygen (which may contain some air), air, oxygen enriched air, oxygen-containing gaseous compounds (e.g., NO), oxygen-containing mixtures (e.g., $O_2/CO_2$, $O_2/H_2O$, $O_2/H_2O_2/H_2O$), oxy radical generators (e.g., $CH_3OH$, $CH_2O$), hydroxyl radical generators, and the like, or combinations thereof. Oxygen can be introduced into CPO reactor 10 via oxygen line 12, in embodiments, or elsewhere (e.g., along with first portion of hydrocarbons 8A or heat exchanged first portion 8A').

In embodiments, the CPO reactant mixture in CPO reactor 10 can be characterized by a carbon to oxygen (C/O) molar ratio of less than or equal to about 5:1, alternatively less than or equal to about 4:1; alternatively less than or equal to about 3:1; alternatively less than or equal to about 2.6:1, alternatively less than or equal to about 2.4:1, alternatively less than or equal to about 2.2:1, alternatively less than or equal to about 2:1, alternatively less than or equal to about 1.9:1, alternatively less than or equal to about 1.8:1, alternatively less than or equal to about 1.75:1, alternatively greater than or equal to about 1.4:1; alternatively greater than or equal to about 2:1, alternatively greater than or equal to about 2.2:1, alternatively greater than or equal to about 2.4:1, alternatively greater than or equal to about 2.6:1, alternatively from about 0.5:1 to about 5:1; alternatively from about 1.4:1 to about 5:1; alternatively from about 0.5:1 to about 3:1, alternatively from about 0.7:1 to about 2.5:1, alternatively from about 0.9:1 to about 2.2:1, alternatively from about 1:1 to about 2:1, alternatively from about 1.1:1 to about 1.9:1, alternatively from about 1.5:1 to about 2.5:1, alternatively from about 1.6:1 to about 2.5:1, alternatively from about 2:1 to about 3:1, alternatively from about 2.2:1 to about 3:1, alternatively from about 2.4:1 to about 3:1, or alternatively from about 2.6:1 to about 3:1, wherein the C/O molar ratio refers to the total moles of carbon (C) of hydrocarbons in the reactant mixture divided by the total moles of oxygen ($O_2$) in the reactant mixture.

For example, when the only source of carbon in the CPO reactant mixture in CPO reactor 10 is $CH_4$ (e.g., introduced via first hydrocarbon portion 8A of hydrocarbons in process portion 5A), the $CH_4/O_2$ molar ratio is the same as the C/O molar ratio. As another example, when the CPO reactant mixture contains other carbon sources besides $CH_4$, such as ethane ($C_2H_6$), propane ($C_3H_8$), butanes ($C_4H_{10}$), etc., the C/O molar ratio accounts for the moles of carbon in each compound (e.g., 2 moles of C in 1 mole of $C_2H_6$, 3 moles of C in 1 mole of $C_3H_8$, 4 moles of C in 1 mole of $C_4H_{10}$, etc.). As will be appreciated by one of skill in the art, and with the help of this disclosure, the C/O molar ratio in the CPO reactant mixture can be adjusted along with other reactor process parameters (e.g., temperature, pressure, flow velocity, etc.) to provide for a syngas with a desired composition (e.g., a syngas with a desired $H_2/CO$ molar ratio; a syngas with a desired $CO_2$ content; etc.). The C/O molar ratio in the CPO reactant mixture can be adjusted to provide for a decreased amount of unconverted hydrocarbons in the syngas. The C/O molar ratio in the CPO reactant mixture can be adjusted based on the CPO effluent temperature in order to decrease (e.g., minimize) the unconverted hydrocarbons content of the syngas in CPO reactor effluent 15A. As will be appreciated by one of skill in the art, and with the help of this disclosure, when the syngas is further used in a methanol production process, unconverted hydrocarbons present in the syngas can undesirably accumulate in a methanol reaction loop, thereby decreasing the efficiency of the methanol production process.

In embodiments, a CPO reactor 10 suitable for use in the present disclosure (e.g., CPO reactor 10) can comprise a tubular reactor, a continuous flow reactor, a fixed bed reactor, a fluidized bed reactor, a moving bed reactor, a circulating fluidized bed reactor (e.g., a riser type reactor), a bubbling bed reactor, an ebullated bed reactor, a rotary kiln reactor, and the like, or combinations thereof. In some embodiments, the CPO reactor 10 can comprise a circulating fluidized bed reactor, such as a riser type reactor.

In some embodiments, the CPO reactor 10 can be characterized by at least one CPO operational parameter selected from the group consisting of a CPO reactor temperature (e.g., CPO catalyst bed temperature); CPO feed temperature (e.g., CPO reactant mixture temperature); target CPO effluent temperature; a CPO pressure (e.g., CPO reactor pressure); a CPO contact time (e.g., CPO reactor contact time); a C/O molar ratio in the CPO reactant mixture; a steam to carbon (S/C) molar ratio in the CPO reactant mixture, wherein the S/C molar ratio refers to the total moles of water ($H_2O$) in the reactant mixture divided by the total moles of carbon (C) of hydrocarbons in the reactant mixture; and combinations thereof. For purposes of the disclosure herein, the CPO effluent temperature is the temperature of the syngas (e.g., syngas effluent; first syngas 15A) measured at the point where the syngas exits the CPO reactor (CPO reactor 10), e.g., a temperature of the syngas measured at a CPO reactor outlet, a temperature of the syngas effluent, a temperature of the exit syngas effluent. For purposes of the disclosure herein, the CPO effluent temperature (e.g., target CPO effluent temperature) is considered an operational parameter. As will be appreciated by one of skill in the art, and with the help of this disclosure, the choice of operational parameters for the CPO reactor such as CPO feed temperature; CPO pressure; CPO contact time; C/O molar ratio in the CPO reactant mixture; S/C molar ratio in the CPO reactant mixture; etc. determines the temperature of the syngas effluent (e.g., CPO reactor effluent syngas 15A), as well as the composition of the syngas effluent (e.g., syngas in CPO reactor effluent 15A). Further, and as will be appreciated by one of skill in the art, and with the help of this disclosure, monitoring the CPO effluent temperature can provide feedback for changing other operational parameters (e.g., CPO feed temperature; CPO pressure; CPO contact time; C/O molar ratio in the CPO reactant mixture; S/C molar ratio in the CPO reactant mixture; etc.) as necessary for the CPO effluent temperature to match the target CPO effluent temperature. Furthermore, and as will be appreciated by one of skill in the art, and with the help of this disclosure, the target CPO effluent temperature is the desired CPO effluent temperature, and the CPO effluent temperature (e.g., measured CPO effluent temperature, actual CPO effluent temperature) may or may not coincide with the target CPO effluent temperature. In embodiments where the CPO effluent temperature is different from the target CPO effluent temperature, one or more CPO operational parameters (e.g., CPO feed temperature; CPO pressure; CPO contact time; C/O molar ratio in the CPO reactant mixture; S/C molar ratio in the CPO reactant mixture; etc.) can be adjusted (e.g., modified) in order for the CPO effluent temperature to match (e.g., be the same with, coincide with) the target CPO effluent temperature. The CPO reactor 10 can be operated under any suitable operational parameters that can provide for a syngas with a desired composition (e.g., a syngas with a desired $H_2/CO$ molar ratio; a syngas with a desired $CO_2$ content; etc.).

The CPO reactor 10 can be characterized by a CPO feed temperature of from about 25° C. to about 600° C., alternatively from about 25° C. to about 500° C., alternatively from about 25° C. to about 400° C., alternatively from about 50° C. to about 400° C., alternatively from about 100° C. to about 400° C., or alternatively less than or equal to about 550, 540, or 535° C.

The CPO reactor 10 can be characterized by a CPO effluent temperature (e.g., target CPO effluent temperature) of greater than or equal to about 300° C., greater than or equal to about 600° C., alternatively greater than or equal to about 700° C., alternatively greater than or equal to about 750° C., alternatively greater than or equal to about 800° C., alternatively greater than or equal to about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

In embodiments, the CPO reactor 10 can be characterized by any suitable reactor temperature and/or catalyst bed temperature. For example, the CPO reactor 10 can be characterized by a reactor temperature and/or catalyst bed temperature of greater than or equal to about 300° C., alternatively greater than or equal to about 600° C., alternatively greater than or equal to about 700° C., alternatively greater than or equal to about 750° C., alternatively greater than or equal to about 800° C., alternatively greater than or equal to about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

The CPO reactor 10 can be operated under any suitable temperature profile that can provide for a syngas with a desired composition (e.g., a syngas with a desired $H_2/CO$ molar ratio; a syngas with a desired $CO_2$ content; etc.). The CPO reactor 10 can be operated under adiabatic conditions, non-adiabatic conditions, isothermal conditions, near-isothermal conditions, etc. For purposes of the disclosure herein, the term "non-adiabatic conditions" refers to process conditions wherein a reactor is subjected to external heat exchange or transfer (e.g., the reactor is heated; or the reactor is cooled), which can be direct heat exchange and/or indirect heat exchange. As will be appreciated by one of skill in the art, and with the help of this disclosure, the terms "direct heat exchange" and "indirect heat exchange" are known to one of skill in the art. By contrast, the term "adiabatic conditions" refers to process conditions wherein a reactor is not subjected to external heat exchange (e.g., the reactor is not heated; or the reactor is not cooled). Generally, external heat exchange implies an external heat exchange system (e.g., a cooling system; a heating system) that requires energy input and/or output. External heat transfer can also result from heat loss from the catalyst bed (or reactor) due to radiation, conduction or convection. For example, this heat exchange from the catalyst bed can be to the external environment or to the reactor zones before and after the catalyst bed.

For purposes of the disclosure herein, the term "isothermal conditions" refers to process conditions (e.g., CPO operational parameters) that allow for a substantially constant temperature of the reactor and/or catalyst bed (e.g., isothermal temperature) that can be defined as a temperature that varies by less than about ±10° C., alternatively less than about ±9° C., alternatively less than about ±8° C., alternatively less than about ±7° C., alternatively less than about ±6° C., alternatively less than about ±5° C., alternatively less than about ±4° C., alternatively less than about ±3° C., alternatively less than about ±2° C., or alternatively less than about ±1° C. across the reactor and/or catalyst bed, respectively.

Further, for purposes of the disclosure herein, the term "isothermal conditions" refers to process conditions (e.g., CPO operational parameters) effective for providing for a syngas with a desired composition (e.g., a desired $H_2/CO$ molar ratio; a desired $CO_2$ content; etc.), wherein the isothermal conditions comprise a temperature variation of less than about ±10° C. across the reactor and/or catalyst bed. In embodiments, CPO reactor 10 can be operated under any suitable operational parameters that can provide for isothermal conditions.

For purposes of the disclosure herein, the term "near-isothermal conditions" refers to process conditions (e.g., CPO operational parameters) that allow for a fairly constant temperature of the reactor and/or catalyst bed (e.g., near-isothermal temperature), which can be defined as a temperature that varies by less than about ±100° C., alternatively less than about ±90° C., alternatively less than about ±80° C., alternatively less than about ±70° C., alternatively less than about ±60° C., alternatively less than about ±50° C., alternatively less than about ±40° C., alternatively less than about ±30° C., alternatively less than about ±20° C., alternatively less than about ±10° C., alternatively less than about ±9° C., alternatively less than about ±8° C., alternatively less than about ±7° C., alternatively less than about ±6° C., alternatively less than about ±5° C., alternatively less than about ±4° C., alternatively less than about ±3° C., alternatively less than about ±2° C., or alternatively less than about ±1° C. across the reactor and/or catalyst bed, respectively. In some embodiments, near-isothermal conditions allow for a temperature variation of less than about ±50° C., alternatively less than about ±25° C., or alternatively less than about ±10° C. across the reactor and/or catalyst bed. Further, for purposes of the disclosure herein, the term "near-isothermal conditions" is understood to include "isothermal" conditions.

Furthermore, for purposes of the disclosure herein, the term "near-isothermal conditions" refers to process conditions (e.g., CPO operational parameters) effective for providing for a syngas with a desired composition (e.g., a desired $H_2/CO$ molar ratio; a desired $CO_2$ content; etc.), wherein the near-isothermal conditions comprise a temperature variation of less than about ±100° C. across the reactor and/or catalyst bed.

In embodiments, a process as disclosed herein can comprise conducting the CPO reaction under near-isothermal conditions to produce syngas, wherein the near-isothermal conditions comprise a temperature variation of less than about ±100° C. across the reactor and/or catalyst bed. In embodiments, the CPO reactor 10 can be operated under any suitable operational parameters that can provide for near-isothermal conditions.

Near-isothermal conditions can be provided by a variety of process and catalyst variables, such as temperature (e.g., heat exchange or heat transfer), pressure, gas flow rates, reactor configuration, catalyst bed configuration, catalyst bed composition, reactor cross sectional area, feed gas staging, feed gas injection, feed gas composition, and the like, or combinations thereof. Generally, and without wishing to be limited by theory, the terms "heat transfer" or "heat exchange" refer to thermal energy being exchanged or transferred between two systems (e.g., two reactors, such as a CPO reactor and a cracking reactor), and the terms "heat transfer" or "heat exchange" are used interchangeably for purposes of the disclosure herein.

In some embodiments, achieving a target CPO effluent temperature and/or near-isothermal conditions can be provided by heat exchange or heat transfer. The heat exchange can comprise heating the reactor; or cooling the reactor. In embodiments, achieving a target CPO effluent temperature and/or near-isothermal conditions can be provided by cooling the reactor. In another embodiment, achieving a target CPO effluent temperature and/or near-isothermal conditions can be provided by heating the reactor.

In some embodiments, achieving a target CPO effluent temperature and/or near-isothermal conditions can be provided by direct heat exchange and/or indirect heat exchange. As will be appreciated by one of skill in the art, and with the help of this disclosure, the terms "direct heat exchange" and "indirect heat exchange" are known to one of skill in the art.

The heat exchange can comprise external heat exchange, external coolant fluid cooling, reactive cooling, liquid nitrogen cooling, cryogenic cooling, electric heating, electric arc heating, microwave heating, radiant heating, natural gas combustion, solar heating, infrared heating, use of a diluent in the CPO reactant mixture, and the like, or combinations thereof. For example, reactive cooling can be effected by carrying out an endothermic reaction in a cooling coil/jacket associated with (e.g., located in) the reactor.

In some embodiments, achieving a target CPO effluent temperature and/or near-isothermal conditions can be provided by removal of process heat from the CPO reactor. In other embodiments, achieving a target CPO effluent temperature and/or near-isothermal conditions can be provided by supplying heat to the CPO reactor. As will be appreciated by one of skill in the art, and with the help of this disclosure, a CPO reactor may need to undergo both heating and cooling in order to achieve a target CPO effluent temperature and/or near-isothermal conditions.

In embodiments, the heat exchange or heat transfer can comprise introducing a cooling agent, such as a diluent, into the reactor (e.g., CPO reactor 10), to decrease the reactor temperature and/or the catalyst bed temperature, while increasing a temperature of the cooling agent and/or changing the phase of the cooling agent. The cooling agent can be reactive or non-reactive. The cooling agent can be in liquid state and/or in vapor state. As will be appreciated by one of skill in the art, and with the help of this disclosure, the cooling agent can act as a flammability retardant; for example by reducing the temperature inside the reactor, by changing the gas mixture composition, by reducing the combustion of hydrocarbons to carbon dioxide; etc.

In some embodiments, the CPO reactant mixture in CPO reactor 10 can further comprise a diluent, wherein the diluent contributes to achieving a target CPO effluent temperature and/or near-isothermal conditions via heat exchange, as disclosed herein. The diluent can comprise water, steam, inert gases (e.g., argon), nitrogen, carbon dioxide, and the like, or combinations thereof. Generally, the diluent is inert with respect to the CPO reaction, e.g., the diluent does not participate in the CPO reaction. However, and as will be appreciated by one of skill in the art, and with the help of this disclosure, some diluents (e.g., water, steam, carbon dioxide, etc.) might undergo chemical reactions other than the CPO reaction within the reactor, and can change the composition of the resulting syngas, as will be described in more detail later herein; while other diluents (e.g., nitrogen ($N_2$), argon (Ar)) might not participate in reactions that change the composition of the resulting syngas. As will be appreciated by one of skill in the art, and with the help of this disclosure, the diluent can be used to vary the composition of the resulting syngas (e.g., the syngas in CPO reactor effluent 15A). The diluent can be present in the CPO reactant mixture in any suitable amount.

The CPO reactor 10 can be characterized by a CPO pressure (e.g., reactor pressure measured at the CPO reactor exit or outlet) of greater than or equal to about 1 barg, alternatively greater than or equal to about 10 barg, alternatively greater than or equal to about 20 barg, alternatively greater than or equal to about 25 barg, alternatively greater than or equal to about 30 barg, alternatively greater than or equal to about 35 barg, alternatively greater than or equal to about 40 barg, alternatively greater than or equal to about 50 barg, alternatively less than about 30 barg, alternatively less than about 25 barg, alternatively less than about 20 barg, alternatively less than about 10 barg, alternatively from about 1 barg to about 90 barg, alternatively from about 1 barg to about 70 barg, alternatively from about 1 barg to about 40 barg, alternatively from about 1 barg to about 30 barg, alternatively from about 1 barg to about 25 barg, alternatively from about 1 barg to about 20 barg, alternatively from about 1 barg to about 10 barg, alternatively from about 20 barg to about 90 barg, alternatively from about 25 barg to about 85 barg, or alternatively from about 30 barg to about 80 barg.

The CPO reactor 10 can be characterized by a CPO contact time of from about 0.001 milliseconds (ms) to about 5 seconds (s), alternatively from about 0.001 ms to about 1 s, alternatively from about 0.001 ms to about 100 ms, alternatively from about 0.001 ms to about 10 ms, alternatively from about 0.001 ms to about 5 ms, or alternatively from about 0.01 ms to about 1.2 ms. Generally, the contact time of a reactor comprising a catalyst refers to the average amount of time that a compound (e.g., a molecule of that compound) spends in contact with the catalyst (e.g., within the catalyst bed), e.g., the average amount of time that it takes for a compound (e.g., a molecule of that compound) to travel through the catalyst bed. In some embodiments, the CPO reactor 10 can be characterized by a contact time of from about 0.001 ms to about 5 ms, or alternatively from about 0.01 ms to about 1.2 ms.

All of the CPO operational parameters disclosed herein are applicable throughout all of the embodiments disclosed herein, unless otherwise specified. As will be appreciated by one of skill in the art, and with the help of this disclosure, each CPO operational parameter can be adjusted to provide for a desired syngas quality (e.g., of CPO reactor effluent 15A), such as a syngas with a desired composition (e.g., a syngas with a desired $H_2/CO$ molar ratio; a syngas with a desired $CO_2$ content; etc.). For example, the CPO operational parameters can be adjusted to provide for an increased $H_2$ content of the syngas. As another example, the CPO operational parameters can be adjusted to provide for a decreased $CO_2$ content of the syngas. As yet another example, the CPO operational parameters can be adjusted to provide for a decreased unreacted hydrocarbons (e.g., unreacted $CH_4$) content of the syngas.

In embodiments, the CPO reactor 10 is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 1.4:1 to about 5:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0 to about 2:1, wherein the S/C molar ratio refers to the total moles of water ($H_2O$) in the reactant mixture divided by the total moles of carbon (C) of hydrocarbons in the reactant mixture; and combinations thereof. In embodiments, the CPO reactor 10 is characterized by a steam to carbon (S/C) molar ratio in the CPO reactant mixture of from about 0.05:1 to about 1:1, from about 0.1:1 to about 2:1, from about 0.1:1 to about 2:1, or equal to about 0.1, 0.2, 0.3, 0.4, 0.5, 0.6, 0.7, 0.8, 0.9, or 1.0.

The CPO reaction is an exothermic reaction (e.g., heterogeneous catalytic reaction; exothermic heterogeneous catalytic reaction) that is generally conducted in the presence of a CPO catalyst comprising a catalytically active metal, i.e., a metal active for catalyzing the CPO reaction. The catalytically active metal can comprise a noble metal (e.g., Pt, Rh, Ir, Pd, Ru, Ag, and the like, or combinations thereof); a non-noble metal (e.g., Ni, Co, V, Mo, P, Fe, Cu, and the like, or combinations thereof); rare earth elements (e.g., La, Ce, Nd, Eu, and the like, or combinations thereof); oxides thereof; and the like; or combinations thereof. Generally, a noble metal is a metal that resists corrosion and oxidation in a water-containing environment. As will be appreciated by one of skill in the art, and with the help of this disclosure, the components of the CPO catalyst (e.g., metals such as noble metals, non-noble metals, rare earth elements) can be either phase segregated or combined within the same phase.

In embodiments, the CPO catalysts suitable for use in the present disclosure can be supported catalysts and/or unsupported catalysts. In some embodiments, the supported catalysts can comprise a support, wherein the support can be catalytically active (e.g., the support can catalyze a CPO reaction). For example, the catalytically active support can comprise a metal gauze or wire mesh (e.g., Pt gauze or wire mesh); a catalytically active metal monolithic catalyst; etc. In other embodiments, the supported catalysts can comprise a support, wherein the support can be catalytically inactive (e.g., the support cannot catalyze a CPO reaction), such as $SiO_2$; silicon carbide (SiC); alumina; a catalytically inactive monolithic support; etc. In yet other embodiments, the supported catalysts can comprise a catalytically active support and a catalytically inactive support.

In some embodiments, a CPO catalyst can be wash coated onto a support, wherein the support can be catalytically active or inactive, and wherein the support can be a monolith, a foam, an irregular catalyst particle, etc.

In some embodiments, the CPO catalyst can be a monolith, a foam, a powder, a particle, etc. Nonlimiting examples of CPO catalyst particle shapes suitable for use in the present disclosure include cylindrical, discoidal, spherical, tabular, ellipsoidal, equant, irregular, cubic, acicular, and the like, or combinations thereof.

In some embodiments, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), zirconium oxide ($ZrO_2$), lanthanum (III) oxide ($La_2O_3$), yttrium (III) oxide ($Y_2O_3$), cerium (IV) oxide ($CeO_2$), zeolites, ZSM-5, perovskite oxides, hydrotalcite oxides, and the like, or combinations thereof.

Without limitation, CPO processes, CPO reactors, CPO catalysts, and CPO catalyst bed configurations suitable for use in the present disclosure are described in more detail in U.S. Provisional Patent Application No. 62/522,910 filed Jun. 21, 2017 (International Application No. PCT/IB2018/054475 filed Jun. 18, 2018) and entitled "Improved Reactor Designs for Heterogeneous Catalytic Reactions;" and U.S. Provisional Patent Application No. 62/521,831 filed Jun. 19, 2017 (International Application No. PCT/IB2018/054470 filed Jun. 18, 2018) and entitled "An Improved Process for Syngas Production for Petrochemical Applications;" each of which is hereby incorporated herein by reference in its entirety for purposes not contrary to this disclosure.

According to this disclosure, a CPO reactor effluent 15A can be recovered from the CPO reactor 10, wherein the CPO reactor effluent 15A comprises hydrogen, carbon monoxide, water, carbon dioxide, and unreacted hydrocarbons (e.g., methane). In embodiments, the CPO reactor effluent 15A can be characterized by an M ratio of greater than or equal to about 1.5, alternatively greater than or equal to about 1.6, alternatively greater than or equal to about 1.7, alternatively greater than or equal to about 1.8, alternatively greater than or equal to about 1.84, alternatively greater than or equal to about 1.9, alternatively from about 1.5 to about 1.95, alternatively from about 1.7 to about 2.3, alternatively from about 1.8 to about 2.2, or alternatively from about 1.9 to about 2.2.

The CPO reactor effluent 15A as disclosed herein can be characterized by a $H_2/CO$ molar ratio of greater than about 1.7, alternatively greater than about 1.8, alternatively greater than about 1.9, alternatively greater than about 2.0, or alternatively greater than about 2.1. In some embodiments, the CPO reactor effluent syngas 15A as disclosed herein can be characterized by a $H_2/CO$ molar ratio of from about 1.7 to about 2.3, alternatively from about 1.75 to about 1.81, alternatively from about 1.8 to about 2.2, or alternatively from about 1.9 to about 2.1.

In embodiments, the CPO reactor effluent 15A can have a $CO_2$ content of less than about 10 mol %, less than about 9 mol %, less than about 8 mol %, less than about 7 mol %, alternatively less than about 6 mol %, alternatively less than about 5 mol %, alternatively less than about 4 mol %, alternatively less than about 3 mol %, alternatively less than about 2 mol %, alternatively less than about 1 mol %, alternatively greater than about 0.1 mol %, alternatively greater than about 0.25 mol %, alternatively greater than about 0.5 mol %, alternatively from about 0.1 mol % to about 7 mol %, alternatively from about 0.25 mol % to about 6 mol %, or alternatively from about 0.5 mol % to about 5 mol %.

According to this disclosure, an SMR reactor effluent 15B can be recovered from the SMR reactor 20, wherein the SMR reactor effluent 15B comprises hydrogen, carbon monoxide, water, carbon dioxide, and unreacted hydrocarbons (e.g., methane). The SMR reactor effluent 15B is characterized by a $H_2/CO$ molar ratio of the SMR reactor effluent 15B that is greater than the $H_2/CO$ molar ratio of the CPO reactor effluent 15A; and the SMR reactor effluent 15B is characterized by an M ratio of the SMR reactor effluent 15B that is greater than the M ratio of the CPO reactor effluent 15A. In embodiments, the SMR reactor effluent 15B can be characterized by an M ratio of greater than or equal to about 1.5, alternatively greater than or equal to about 1.6, alternatively greater than or equal to about 1.7, alternatively greater than or equal to about 1.8, alternatively greater than or equal to about 1.84, alternatively greater than or equal to about 1.9, alternatively from about 1.5 to about 1.95, alternatively from about 1.7 to about 2.3, alternatively from about 1.8 to about 2.2, or alternatively from about 1.9 to about 2.2.

The SMR reactor effluent 15B as disclosed herein can be characterized by a $H_2/CO$ molar ratio of greater than about 1.7, alternatively greater than about 1.8, alternatively greater than about 1.9, alternatively greater than about 2.0, or alternatively greater than about 2.1. In some embodiments, the SMR reactor effluent 15B as disclosed herein can be characterized by a $H_2/CO$ molar ratio of from about 1.7 to about 2.3, alternatively from about 1.75 to about 1.81, alternatively from about 1.8 to about 2.2, or alternatively from about 1.9 to about 2.1.

In embodiments, the SMR reactor effluent 15B can have a $CO_2$ content of less than about 10 mol %, less than about 9 mol %, less than about 8 mol %, less than about 7 mol %, alternatively less than about 6 mol %, alternatively less than about 5 mol %, alternatively less than about 4 mol %, alternatively less than about 3 mol %, alternatively less than about 2 mol %, alternatively less than about 1 mol %, alternatively greater than about 0.1 mol %, alternatively greater than about 0.25 mol %, alternatively greater than about 0.5 mol %, alternatively from about 0.1 mol % to about 7 mol %, alternatively from about 0.25 mol % to about 6 mol %, or alternatively from about 0.5 mol % to about 5 mol %.

The process of this disclosure can comprise (c) contacting at least a portion of the CPO reactor effluent 15A with at least a portion of the SMR reactor effluent 15B to yield a combined syngas 15C (optionally either upstream or downstream of a first heat exchanger HE1 and/or a third heat exchanger HE3), wherein the combined syngas of the combined CPO and SMR reactor effluents, 15A and 15B, respectively, is characterized by a $H_2/CO$ molar ratio of the combined syngas, and wherein the combined syngas is characterized by an M ratio of the syngas. The H2/CO molar ratio of the combined syngas 15C is greater than the H2/CO molar ratio of the CPO reactor effluent 15A and less than the H2/CO molar ratio of the SMR reactor effluent 15B. The M ratio of the combined syngas 15C is greater than the M ratio of the CPO reactor effluent 15A and less than the M ratio of the SMR reactor effluent 15B.

The system can thus comprise one or more flow lines configured to combine at least a portion of the CPO reactor effluent 15A with at least a portion of the SMR reactor effluent 15B to provide a combined syngas stream 15C. The one or more flow lines can be positioned upstream or downstream of first heat exchanger HE1 and/or third heat exchanger HE3, in embodiments.

In embodiments, the combined syngas 15C (and the syngas 15D, 15E, and 15E', described further hereinbelow) can be characterized by an M ratio of greater than or equal to about 1.9, 1.95, or 2.0, from about 1.9 to about 2.5, alternatively from about 1.9 to about 2.2, alternatively from about 1.95 to about 2.1, or alternatively from about 2 to about 2.1. In embodiments, the combined syngas 15C/15D/15E/15E' can be characterized by a $H_2/CO$ molar ratio of greater than or equal to about 1.8, 1.9, or 2, or from about 1.8 to about 2, alternatively from about 1.9 to about 2, or alternatively from about 1.8 to about 2.5.

In embodiments, water can be condensed and separated from at least a portion of the CPO reactor effluent 15A, at least a portion of the SMR reactor effluent 15B, or a combination thereof (e.g., a combined syngas stream 15C comprising at least a portion of CPO reactor effluent 15A and at least a portion of SMR reactor effluent 15B), e.g., in a condenser. In embodiments, the CPO reactor effluent 15A and/or the SMR reactor effluent 15B can be subjected to processing, such as the recovery of unreacted hydrocarbons, diluent, water, etc. In embodiments, a process as disclosed herein can further comprise: (i) recovering at least a portion of the unreacted hydrocarbons from the CPO reactor effluent 15A and/or the SMR reactor effluent 15B to yield recovered hydrocarbons, and (ii) recycling at least a portion of the recovered hydrocarbons to the CPO reactor 10 and/or the SMR reactor 20. As will be appreciated by one of skill in the art, and with the help of this disclosure, although fairly high conversions can be achieved in CPO and SMR processes (e.g., CPO conversions of greater than or equal to about 90%), the unconverted hydrocarbons can be recovered and recycled back to the CPO reactor 10 and/or the SMR reactor 20, in embodiments.

In embodiments, a process of this disclosure further comprises cooling the CPO reactor effluent 15A, the SMR reactor effluent 15B, or the combined syngas stream 15C by heating the hydrocarbons of first hydrocarbon portion 8A, the hydrocarbons of second hydrocarbon portion 8B, or hydrocarbon stream 8 comprising first hydrocarbon portion 8A and second hydrocarbon portion 8B prior to splitting thereof to feed CPO reactor 10 and SMR reactor 20, while cooling the CPO reactor effluent 15A, the SMR reactor effluent 15B, or the combined syngas stream 15C, respectively, by heat exchange in a first heat exchanger HE1 to yield heated hydrocarbons and a first cooled reactor effluent 15D. In embodiments, the heated hydrocarbons (e.g., heated first hydrocarbon portion 8A, heated second hydrocarbon portion 8B) are introduced directly into CPO reactor 10 and/or SMR reactor 20, respectively. In embodiments, a combined hydrocarbon stream 5A is heated to provide heated hydrocarbon stream 5A', which is split to provide first hydrocarbon portion 8A and second hydrocarbon portion 8B, which are fed directly to CPO reactor 10 and SMR reactor 20, respectively. In alternate embodiments, the hydrocarbons of process hydrocarbons 5A are heated to provide heated process hydrocarbons 5A' prior to desulfurization thereof. In embodiments, the heated process hydrocarbons 5A' comprise one or more sulfur-containing compounds, and the process comprises removing at least a portion of the sulfur-containing compounds from the heated process hydrocarbons 5A' to yield desulfurized process hydrocarbon stream 8, which can be split to provide first hydrocarbon portion 8A and second hydrocarbon portion 8B. In embodiments, first hydrocarbon portion 8A is introduced directly into CPO reactor 10, while, in alternative embodiments, first hydrocarbon portion 8A is introduced into CPO reactor 10 following heat exchange in a second heat exchanger HE2, as described further below. Thus, in embodiments, heating water while cooling the CPO reactor effluent 15A and/or the SMR reactor effluent 15B (e.g., combined syngas 15C) by heat exchange in a first heat exchanger HE1 yields a (first) cooled reactor effluent 15D.

In embodiments, the herein disclosed process further comprises cooling at least a portion (e.g., the first hydrocarbon portion 8A) of the desulfurized hydrocarbons 8. For example, in embodiments, at least a portion of the desulfurized hydrocarbons 8 are cooled by heating water 9 while cooling the desulfurized hydrocarbons 8 (e.g., the first hydrocarbon portion 8A) by heat exchange in a second heat exchanger HE2 to yield steam 11 and cooled desulfurized first hydrocarbon portion 8A'. In embodiments, at least a portion of the cooled desulfurized first hydrocarbon portion 8A' and optionally at least a portion 11A of the steam 11 are fed to the CPO reactor 10 in step (a). In embodiments, at least a portion 11B of the steam 11 is fed to SMR reactor 20 in step (b).

In embodiments, cooling the CPO reactor effluent 15A, the SMR reactor effluent 15B, or the combined syngas 15C further comprises heating water 16 while cooling the first cooled reactor effluent 15D by heat exchange in a third heat exchanger HE3 to yield steam 17 and a second cooled reactor effluent 15E. In embodiments, at least a portion of the second cooled reactor effluent 15E is fed to a downstream methanol synthesis reactor 40, as described further hereinbelow. The steam 17 can be high pressure steam. In embodiments, at least a portion 17A of the steam 17 is utilized to power a steam-driven compressor, such as compressor 30 described further hereinbelow.

In embodiments, a process for producing methanol as disclosed herein can comprise a step of feeding at least a portion of the syngas 15E to a methanol synthesis reactor or 'methanol reactor' 40 to produce a methanol reactor effluent stream 45. The methanol reactor effluent stream 45 comprises methanol, water, $H_2$, CO, $CO_2$, and hydrocarbons. The methanol synthesis reactor 40 can comprise any reactor suitable for a methanol synthesis reaction from CO and $H_2$, such as for example a trickle bed reactor, a fluidized bed reactor, a slurry reactor, a loop reactor, a cooled multi tubular reactor, and the like, or combinations thereof.

Generally, CO and $H_2$ can be converted into methanol ($CH_3OH$), for example as represented by Equation (3):

(3)

$CO_2$ and $H_2$ can also be converted to methanol, for example as represented by Equation (4):

(4)

Without wishing to be limited by theory, the lower the $CO_2$ content of the syngas 15E, the lower the amount of water produced in the methanol reactor 40. As will be appreciated by one of skill in the art, and with the help of this disclosure, syngas produced by SMR has a fairly high content of hydrogen (as compared to the hydrogen content of syngas produced by CPO), and a syngas with an elevated hydrogen content can promote the $CO_2$ conversion to methanol, for example as represented by Equation (4), which in turn can lead to an increased water content in a crude methanol stream (e.g., crude methanol stream 55, described hereinbelow).

Methanol synthesis from CO, $CO_2$ and $H_2$ is a catalytic process, and is most often conducted in the presence of copper based catalysts. The methanol synthesis reactor 40 can comprise a methanol production catalyst, such as any suitable commercial catalyst used for methanol synthesis. Nonlimiting examples of methanol production catalysts suitable for use in the methanol reactor 40 in the current disclosure include Cu, Cu/ZnO, $Cu/ThO_2$, $Cu/Zn/Al_2O_3$, $Cu/ZnO/Al_2O_3$, Cu/Zr, and the like, or combinations thereof.

In embodiments, a process for producing methanol as disclosed herein can comprise a step of compressing at least a portion of the syngas 15E in a syngas compressor 30 to yield a compressed syngas 15E', and feeing at least a portion of the compressed syngas 15E' to the methanol reactor 40. In embodiments, the compressor 30 is a steam-driven compressor, and at least a portion 17A of the (e.g., HP) steam 17 is used in a turbine for the steam-driven compressor. In embodiments, the compressor 30 is a steam-driven compressor, and at least a portion of the fuel portion 5B of the hydrocarbon feed 5 is utilized to provide steam for powering the steam-driven compressor. In embodiments, steam (e.g., additional or alternate steam) is generated via combustion of alternate hydrocarbons, and the steam is further used to power the steam-driven compressor. As noted above, in embodiments, the syngas 15E and/or compressed syngas 15E' fed to methanol synthesis reactor 40 is characterized by a $H_2/CO$ molar ratio of greater than or equal to about 1.8 and/or an M ratio of greater than or equal to about 1.9, 1.95, or 2.0.

In embodiments, methanol reactor 40 utilizes a series (e.g., 3, 4, or 5) of quenched bed reactors, and cold feed is mixed with the exit gas from each bed to lower the gas temperature before the feed is passed to the subsequent bed. Due to increased carbon monoxide concentration in the methanol reactor loop according to this disclosure, the temperature of the exit gas from each bed may be higher than in methanol synthesis plants employing SMR alone. Accordingly, in embodiments, the temperature of the cold feed streams injected between the beds can be lowered until an adiabatic operation in the methanol synthesis reactor 40 is achieved.

In embodiments, a process for producing methanol as disclosed herein can comprise a step of introducing at least a portion of the methanol reactor effluent stream 45 to a separator 50 to produce a crude methanol stream 55 and a vapor stream 56, wherein the crude methanol stream 55 comprises methanol and water, and wherein the vapor stream 56 comprises $H_2$, CO, $CO_2$, and hydrocarbons. The methanol reactor effluent stream 45 can be separated into the crude methanol stream 55 and the vapor stream 56 in the gas-liquid separator 50, such as a vapor-liquid separator, flash drum, knock-out drum, knock-out pot, compressor suction drum, etc.

In embodiments, a process for producing methanol as disclosed herein can comprise a step of separating at least a portion of the crude methanol stream 55 in a distillation unit 60 into a methanol stream 65 and a water stream 66. The distillation unit 60 can comprise one or more distillation columns. The water stream 66 comprises water and residual methanol. Generally, the one or more distillation columns can separate components of the crude methanol stream 55 based on their boiling points. As will be appreciated by one of skill in the art, and with the help of this disclosure, the higher the water content of the crude methanol stream 55, the more distillation columns are necessary to purify the methanol.

In embodiments, the methanol stream 65 can comprise methanol in an amount of greater than or equal to about 95 wt. %, alternatively greater than or equal to about 97.5 wt. %, alternatively greater than or equal to about 99 wt. %, or alternatively greater than or equal to about 99.9 wt. %, based on the total weight of the methanol stream 65.

In embodiments, a process for producing methanol as disclosed herein can comprise a step of purging and/or using as fuel a first portion 56' of the vapor stream 56, and recycling a second portion 56" of the vapor stream 56 to the methanol reactor 40. In embodiments, the second portion 56" of the vapor stream 56 is from about 90 weight percent (wt %) % to about 99 wt %, from about 94 wt % to about 97 wt %, or from about 91 wt % to about 98 wt % of the vapor stream 56, based on the total weight of the vapor stream 56. In embodiments, the first portion 56' of the vapor stream 56 that is purged (or sent for use as fuel) is from about 1 weight percent (wt %) % to about 10 wt %, from about 2 wt % to about 9 wt %, or from about 3 wt % to about 6 wt % of the vapor stream 56.

First portion 56' of vapor stream 56 can be divided into a first first portion 56'A and a second first portion 56'B. At least a portion of first first portion 56'A can be recycled to CPO reactor 10, for example via process portion 5A of the hydrocarbon feed 5 and/or first portion 8A of hydrocarbons. At least a portion of second first portion 56'B can be utilized as fuel for heating SMR reactor 20 and/or for steam generation. First first portion 56'A can comprise from 0 to 100% of the flow of first portion 56'; second first portion 56'B can comprise from 0 to 100% of the flow of first portion 56'. For example, in embodiments, the flow of first first portion 56'A comprises 0, 25, 60, or 100% of the flow of first portion 56', and the flow of second first portion 56'B comprises the remaining 100, 75, 40, or 0% of the flow of first portion 56'.

In embodiments, the syngas and/or methanol synthesis system and process of this disclosure exclude an additional hydrogen enrichment (e.g., WGS) and/or $CO_2$ removal step or apparatus prior to downstream chemical (e.g., methanol) synthesis. In embodiments, the methanol reactor 40 is characterized by a methanol reactor volume that is decreased (e.g., for the same methanol production) when compared to the volume of a methanol reactor used in an otherwise similar process that produces methanol from syngas generated via an SMR reactor without a CPO reactor; wherein the syngas generated via an SMR reactor without a CPO reactor is characterized by a $H_2/CO$ molar ratio that is greater than the $H_2/CO$ molar ratio of the syngas in step (c) (e.g., the combined syngas 15C).

In embodiments, the methanol reactor 40 is characterized by a methanol reactor volume that is the same as the volume of a methanol reactor used in an otherwise similar process that produces methanol from syngas generated via an SMR reactor without a CPO reactor; wherein the syngas generated via an SMR reactor without a CPO reactor is characterized by a $H_2/CO$ molar ratio that is greater than the $H_2/CO$ molar ratio of the syngas in step (c) (e.g., the combined syngas 15C), and the herein disclosed process produces a greater amount of methanol for a given amount of hydrocarbon feed 5.

In embodiments, a process for producing methanol as disclosed herein can advantageously display improvements in one or more process characteristics when compared to conventional processes. In embodiments, a methanol synthesis process of this disclosure provides for an increased carbon efficiency, a reduced methanol reactor size due to lower syngas flow (or increased methanol production for a same methanol reactor size), a reduced energy intensity, a higher overall efficiency, a higher chemical carbon efficiency, a reduced syngas compressor duty, a higher methanol loop efficiency, a reduced steam usage, or a combination thereof relative to an otherwise similar process that utilizes solely SMR to generate the syngas for methanol synthesis.

By utilizing CPO, along with SMR, rather than an SMR alone (along with heat integration (e.g., via heat exchangers HE1, HE2, and/or HE3)) to provide a synthesis gas suitable for downstream methanol synthesis, the herein disclosed system and process allow for a reduced energy utilization with minimal capital expenditures for a new or retrofit application. In embodiments, a methanol synthesis plant of this disclosure provides for an energy intensity reduction from an indexed value of from about 90 to 100 MMBTU/ton of methanol to an indexed value of from about 55 to 85 MMBTU/ton of methanol, which represents a reduction of from about 15% to 45%. In embodiments, CPO and SMR are utilized in conjunction to provide a syngas suitable for downstream methanol synthesis (or synthesis of another chemical for which a reduced H2/CO molar ratio is desirable) without the utilization of a hydrogen enrichment mechanism (e.g., without water gas shift (WGS)) and/or without the use of a $CO_2$ rejection mechanism (e.g., without a $CO_2$ separator, e.g., downstream of a WGS reactor).

A process according to this disclosure can generate higher heat from the methanol synthesis reactor 40, which heat can be utilized within the process (e.g., to provide for a boiling feed water reactor and/or to heat the process portion 5A of the hydrocarbon feed 5 prior to desulfurization in desulfurization unit 6).

As will be appreciated by one of skill in the art, and with the help of this disclosure, since the CPO reaction is exothermic, very little heat supply in the form of fuel combustion is needed (e.g., for pre-heating reactants in the reaction mixture that is supplied to a syngas generation section), when compared to conventional steam reforming. As such, the process for producing methanol utilizing CPO syngas as disclosed herein can advantageously generate less $CO_2$ through fuel burning, when compared to the use of solely steam reforming.

Additional advantages of the processes for the production methanol as disclosed herein can be apparent to one of skill in the art viewing this disclosure.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

Example 1

Table 1 shows the results for an existing methanol synthesis process comprising SMR (Comparative Example) and inventive methanol synthesis processes (Inventive Processes A, B, and C) of this disclosure wherein the 20, 40, or 60 wt %, respectively, of the process hydrocarbon feed (5A) is converted to syngas via a CPO reactor 10, while the remaining 80, 60, or 40 wt %, respectively, is converted to syngas in an SMR reactor 20. In the inventive processes, the index fuel natural gas split (e.g., the fuel portion 5B of the hydrocarbon feed 5 (e.g., natural gas) utilized for fuel) was 79.72, 70.86, and 53.14 wt % of the total hydrocarbon feed 5, for the inventive processes A, B, and C, respectively. The purge gas split was 102.4, 101.87, and 101.87 for the inventive processes A, B, and C, respectively. The energy intensity (EI) index as the MMBTU per ton of methanol produced was reduced from 100 MMBTU/ton methanol produced to 83.47, 75.58, and 67.11 MMBTU/ton methanol for the inventive processes A, B, and C, respectively. The loop efficiency index remained substantially unchanged for the inventive processes A, B, and C, relative to the comparative process. As seen in Table 1, the overall efficiency index, the carbon chemical efficiency index, the index production of crude methanol (e.g., crude methanol stream 55 in The FIGURE), the formation of byproduct dimethyl ether (DME), the index package boiler duty, the air separation unit (ASU) duty, and the index inert concentration in the methanol synthesis loop, increased for the inventive processes A, B, and C, relative to the comparative process. As seen in Table 1, the index duty for methanol reactor 40, the index total steam in utility, and the index total duty of the syngas compressor 30 decreased for the inventive processes A, B, and C, relative to the comparative process.

TABLE 1

Data from Example 1

| Item | Existing Process (Comparative Example) | 20 wt % Feed to CPOX (Inventive Process A) | 40 wt % Feed to CPOX (Inventive Process B) | 60 wt % Feed to CPOX (Inventive Process C) |
|---|---|---|---|---|
| Fuel Natural Gas Split (Index) | 100 | 79.72 | 70.86 | 53.14 |
| Purge Gas Split (Index) | 100 | 102.40 | 101.87 | 101.87 |
| EI (MMBTU/ton MeOH) (Index) | 100 | 83.47 | 75.58 | 67.11 |
| Loop Efficiency (Index) | 100 | 102.20 | 100.82 | 99.03 |
| Overall Efficiency (Index) | 100 | 107.00 | 109.52 | 113.21 |
| Carbon Chemical Efficiency (Index) | 100 | 104.82 | 105.88 | 106.54 |
| M-Value Feed (56" + 15E') | 12.52 | 14.42 | 8.76 | 5.30 |
| M-Fresh (15A) | 3.01 | 2.71 | 2.46 | 2.21 |
| Production Crude (MeOH tonnes/day) (Index) | 100 | 106.96 | 109.47 | 113.19 |
| MeOH Reactor Duty (MMBTU/h) (Index) | −100 | −103 | −125.4 | −143.8 |
| Package Boiler Duty (MMBTU/h) (Index) | 100 | 206.01 | 296.46 | 400.89 |
| ASU Duty (MMBTU/ton MeOH) | 100 | 135.36 | 170.01 | 204.37 |
| Inert Conc. in the Loop mol % (Index) | 100 | 117.43 | 119.28 | 122.6 |
| DME Formation (kmol/h) | 100 | 124 | 140.3 | 172.5 |
| Total Steam in Utility (tonne/h) (Index) | 100 | 97.61 | 96.41 | 95.22 |
| Total Syngas Compressor Duty MMBTU/h) (Index) | 100 | 96.31 | 91.80 | 89.16 |
| Total Circulator Duty (MMBTU/h) (Index) | 100 | 124.93 | 85.11 | 62.03 |

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Description

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and processes are described in broader terms of "having", "comprising," "containing," or "including" various components or steps, the compositions and processes can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments Disclosed Herein Include:

A: A process for producing syngas comprising: (a) feeding a catalytic partial oxidation (CPO) reactant mixture to a CPO reactor; wherein the CPO reactant mixture comprises oxygen, a first portion of hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2$/CO) molar ratio of the CPO reactor effluent, and wherein the CPO reactor effluent is characterized by an M ratio of the CPO reactor effluent, wherein the M ratio is a molar ratio defined as ($H_2$—$CO_2$)/(CO+$CO_2$); (b) feeding a steam methane reforming (SMR) reactant mixture to an SMR reactor, wherein the SMR reactant mixture comprises steam and a second portion of hydrocarbons; wherein at least a portion of the SMR reactant mixture reacts, via an SMR reaction, in the SMR reactor to produce an SMR reactor effluent; wherein the SMR reactor effluent comprises hydrogen ($H_2$), carbon monoxide (CO), carbon dioxide ($CO_2$), water, and unreacted hydrocarbons; wherein the SMR reactor effluent is characterized by a $H_2$/CO molar ratio of the SMR reactor effluent that is greater than the $H_2$/CO molar ratio of the CPO reactor effluent; and wherein the SMR reactor effluent is characterized by an M ratio of the SMR reactor effluent that is greater than the M ratio of the CPO reactor effluent; (c) contacting at least a portion of the CPO reactor effluent with at least a portion of the SMR reactor effluent to yield syngas, wherein the syngas is characterized by a $H_2$/CO molar ratio of the syngas, and wherein the syngas is characterized by an M ratio of the syngas; and (d) cooling the syngas; wherein cooling the syngas comprises heating the first portion of hydrocarbons and/or the second portion of hydrocarbons while cooling the syngas by heat exchange in a first heat exchanger to yield a heated first portion of hydrocarbons and/or a heated second portion of hydrocarbons, respectively, and a first cooled syngas; and wherein the heated first portion of hydrocarbons is fed to the CPO reactor in step (a) and/or the heated second portion of hydrocarbons is fed to the SMR reactor in step (b), respectively.

B: A process for producing methanol comprising: (a) heating a feedstream comprising hydrocarbons to yield heated hydrocarbons; (b) optionally removing one or more sulfur-containing compounds from the heated hydrocarbons when present; (c) splitting the heated hydrocarbons into a first portion of hydrocarbons and a second portion of hydrocarbons; (d) feeding a catalytic partial oxidation (CPO) reactant mixture to a CPO reactor; wherein the CPO reactant mixture comprises oxygen, the first portion of hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2$/CO) molar ratio of the CPO reactor effluent, and wherein the CPO reactor effluent is characterized by an M ratio of the CPO reactor effluent, wherein the M ratio is a molar ratio defined as ($H_2$—$CO_2$)/(CO+$CO_2$); (e) feeding a steam methane reforming (SMR) reactant mixture to an SMR reactor, wherein the SMR reactant mixture comprises steam and the second portion of hydrocarbons; wherein at least a portion of the SMR reactant mixture reacts, via an SMR reaction, in the SMR reactor to produce an SMR reactor effluent; wherein the SMR reactor effluent comprises hydrogen ($H_2$), carbon monoxide (CO), carbon dioxide ($CO_2$), water, and unreacted hydrocarbons; wherein the SMR reactor effluent is characterized by a $H_2$/CO molar ratio of the SMR reactor effluent that is greater than the $H_2$/CO molar ratio of the CPO reactor effluent; wherein the SMR reactor effluent is characterized by an M ratio of the SMR reactor effluent that is greater than the M ratio of the CPO reactor effluent; and wherein a weight ratio of the first portion of hydrocarbons to the second portion of hydrocarbons is from about 1:4 to about 3:1; (f) contacting at least a portion of the CPO reactor effluent with at least a portion of the SMR reactor effluent to yield syngas; (g) heating water while cooling the syngas by heat exchange in a heat exchanger to yield steam and a cooled syngas; (h) powering a steam-driven compressor with at least a portion of the steam; (i) compressing at least a portion of the cooled syngas in the steam-driven compressor to yield compressed syngas; (j) introducing at least a portion of the compressed syngas to a methanol reactor to produce a methanol reactor effluent stream; wherein the methanol reactor effluent stream comprises methanol, water, hydrogen, carbon monoxide, carbon dioxide, and hydrocarbons; (k) separating at least a portion of the methanol reactor effluent stream into a crude methanol stream and a vapor stream; wherein the crude methanol stream comprises methanol and water; and wherein the vapor stream comprises hydrogen, carbon monoxide, carbon dioxide, and hydrocarbons; and (l) recycling from about 90 wt. % to about 99 wt. % of the vapor stream, based on the total weight of the vapor stream to the methanol reactor.

C: A system comprising: (a) a catalytic partial oxidation (CPO) reactor operable to convert at least a portion of a CPO reactant mixture comprising oxygen, a first portion of hydrocarbons, and optionally steam, via a CPO reaction, to a CPO reactor effluent comprising hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2$/CO) molar ratio and an M ratio, wherein the M ratio is a molar ratio defined as ($H_2$—$CO_2$)/(CO+$CO_2$); (b) a steam methane reforming (SMR) reactor operable to convert at least a portion of an SMR reactant mixture comprising steam and a second portion of hydrocarbons, via an SMR reaction, to an SMR reactor effluent comprising hydrogen ($H_2$), carbon monoxide (CO), carbon dioxide ($CO_2$), water, and unreacted hydrocarbons; wherein the SMR reactor effluent is characterized by a $H_2$/CO molar ratio that is greater than the $H_2$/CO molar ratio of the CPO reactor effluent, and an M ratio that is greater than the M ratio of the CPO reactor effluent; (c) one or more flow lines configured to combine at least a portion of the CPO reactor effluent with at least a portion of the SMR reactor effluent to provide a combined syngas stream upstream or downstream of a heat exchanger; and (d) the heat exchanger operable to transfer heat from at least a portion of the CPO reactor effluent, at least a portion of the SMR reactor effluent, or the combined syngas stream to the first portion of hydrocarbons, the second portion of hydrocarbons, or a combined hydrocarbon stream comprising the first portion of hydrocarbons and the second portion of hydrocarbons to yield a heated first portion of hydrocarbons, a heated second portion of hydrocarbons, or a heated combined hydrocarbon stream, respectively, wherein the combined syngas stream is characterized by an M ratio of greater than or equal to about 1.7 and/or an $H_2/CO$ molar ratio of greater than or equal to about 1.8.

Each of embodiments A, B, and C may have one or more of the following additional elements: Element 1: wherein the step (d) of cooling the syngas further comprises heating water while cooling the first cooled syngas by heat exchange in a third heat exchanger to yield steam and a second cooled syngas, wherein at least a portion of the steam is used to power a steam-driven compressor. Element 2: wherein at least a portion of the first cooled syngas and/or at least a portion of the second cooled syngas are introduced to the steam-driven compressor to yield compressed syngas. Element 3: further comprising (i) introducing at least a portion of the compressed syngas to a methanol reactor to produce a methanol reactor effluent stream; wherein the methanol reactor effluent stream comprises methanol, water, hydrogen, carbon monoxide, carbon dioxide, and hydrocarbons; and (ii) separating at least a portion of the methanol reactor effluent stream into a crude methanol stream and a vapor stream; wherein the crude methanol stream comprises methanol and water; and wherein the vapor stream comprises hydrogen, carbon monoxide, carbon dioxide, and hydrocarbons. Element 4: wherein a first portion of the vapor stream is recycled to the methanol reactor; and wherein a second portion of the vapor stream is purged, recycled to the CPO reactor as a component of the CPO reactant mixture, and/or used as fuel. Element 5: wherein from 0 to 100% of the second portion of the vapor stream is recycled to the CPO reactor as a component of the CPO reactant mixture and a remainder of the second portion of the vapor stream is used as a fuel for heating the SMR reactor and/or for generating steam. Element 6: wherein the methanol reactor is characterized by a methanol reactor volume that is decreased when compared to the volume of a methanol reactor used in an otherwise similar process that produces methanol from syngas generated via an SMR reactor without a CPO reactor; wherein the syngas generated via an SMR reactor without a CPO reactor is characterized by a $H_2/CO$ molar ratio that is greater than the $H_2/CO$ molar ratio of the syngas in step (c). Element 7: wherein the hydrocarbons comprise methane, natural gas, natural gas liquids, associated gas, well head gas, enriched gas, paraffins, shale gas, shale liquids, fluid catalytic cracking (FCC) off gas, refinery process gases, stack gases, or combinations thereof. Element 8: wherein the hydrocarbons further comprise one or more sulfur-containing compounds. Element 9: wherein at least a portion of the sulfur-containing compounds is removed from the heated second portion of hydrocarbons to yield a desulfurized second portion of hydrocarbons, and wherein the desulfurized second portion of hydrocarbons is fed to the SMR reactor in step (b). Element 10: wherein at least a portion of the sulfur-containing compounds is removed from the heated first portion of hydrocarbons to yield a desulfurized first portion of hydrocarbons, and wherein the desulfurized first portion of hydrocarbons is fed to the CPO reactor in step (a). Element 11: further comprising cooling the desulfurized first portion of hydrocarbons. Element 12: wherein cooling the desulfurized first portion of hydrocarbons comprises heating water while cooling the desulfurized first portion of hydrocarbons by heat exchange in a second heat exchanger to yield steam and a cooled desulfurized first portion of hydrocarbons, and wherein at least a portion of the cooled desulfurized first portion of hydrocarbons is fed to the CPO reactor in step (a). Element 13: wherein at least a portion of the steam produced by the second heat exchanger is fed to the CPO reactor in step (a) and/or the SMR reactor in step (b). Element 14: further comprising (1) heating a feedstream comprising hydrocarbons to yield heated hydrocarbons; (2) optionally removing one or more sulfur-containing compounds from the heated hydrocarbons when present; and (3) splitting the heated hydrocarbons into the first portion of hydrocarbons and the second portion of hydrocarbons. Element 15: wherein a weight ratio of the first portion of hydrocarbons to the second portion of hydrocarbons is from about 1:9 to about 9:1. Element 16: wherein the CPO reactor is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 1.5:1 to about 2.5:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0 to about 2:1, wherein the S/C molar ratio refers to the total moles of water ($H_2O$) in the reactant mixture divided by the total moles of carbon (C) of hydrocarbons in the reactant mixture; and combinations thereof. Element 17: wherein (1) the M ratio of the syngas is equal to or greater than about 1.7; and/or (2) the $H_2/CO$ molar ratio of the syngas is equal to or greater than about 1.8. Element 18: wherein the SMR reactor is characterized by an S/C molar ratio in the SMR reactant mixture of equal to or greater than about 1.5:1. Element 19: further comprising (1) withdrawing a third portion of hydrocarbons from the feedstream prior to step (a), wherein the third portion of hydrocarbons is from about 5 wt. % to about 15 wt. % of the total hydrocarbons of the feedstream, based on the total weight of the total hydrocarbons, and wherein the total hydrocarbons are given by the sum of the first portion of hydrocarbons, the second portion of hydrocarbons, and the third portion of hydrocarbons; and (2) combusting the third portion of hydrocarbons to generate heat for heating the SMR reactor and/or generating additional steam, and wherein at least a portion of the additional steam is used to power the steam-driven compressor. Element 20: further comprising a methanol synthesis reactor operable to produce a methanol reactor effluent stream comprising methanol from at least a portion of the combined syngas stream. Element 21: further comprising another heat exchanger downstream of the heat exchanger and operable to produce steam via heat exchange with the combined syngas stream. Element 22: further comprising a steam-driven compressor upstream of the methanol synthesis reactor and operable to compress the at least a portion of the combined syngas stream, wherein at least a portion of the steam for powering a turbine of the steam-driven compressor comprises the steam produced via heat exchange with the combined syngas stream.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing syngas comprising:
   (a) feeding a catalytic partial oxidation (CPO) reactant mixture to a CPO reactor; wherein the CPO reactant mixture comprises oxygen, a first portion of hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2$/CO) molar ratio of the CPO reactor effluent, and wherein the CPO reactor effluent is characterized by an M ratio of the CPO reactor effluent, wherein the M ratio is a molar ratio defined as ($H_2$-$CO_2$)/(CO+$CO_2$);
   (b) feeding a steam methane reforming (SMR) reactant mixture to an SMR reactor, wherein the SMR reactant mixture comprises steam and a second portion of hydrocarbons; wherein at least a portion of the SMR reactant mixture reacts, via an SMR reaction, in the SMR reactor to produce an SMR reactor effluent; wherein the SMR reactor effluent comprises hydrogen ($H_2$), carbon monoxide (CO), carbon dioxide ($CO_2$), water, and unreacted hydrocarbons; wherein the SMR reactor effluent is characterized by a $H_2$/CO molar ratio of the SMR reactor effluent that is greater than the $H_2$/CO molar ratio of the CPO reactor effluent; and wherein the SMR reactor effluent is characterized by an M ratio of the SMR reactor effluent that is greater than the M ratio of the CPO reactor effluent;
   (c) contacting at least a portion of the CPO reactor effluent with at least a portion of the SMR reactor effluent to yield syngas, wherein the syngas is characterized by a $H_2$/CO molar ratio of the syngas, and wherein the syngas is characterized by an M ratio of the syngas; and
   (d) cooling the syngas; wherein cooling the syngas comprises heating the first portion of hydrocarbons and/or the second portion of hydrocarbons while cooling the syngas by heat exchange in a first heat exchanger to yield a heated first portion of hydrocarbons and/or a heated second portion of hydrocarbons, respectively, and a first cooled syngas; and wherein the heated first portion of hydrocarbons is fed to the CPO reactor in step (a) and/or the heated second portion of hydrocarbons is fed to the SMR reactor in step (b), respectively.

2. The process of claim 1, wherein the step (d) of cooling the syngas further comprises heating water while cooling the first cooled syngas by heat exchange in a third heat exchanger to yield steam and a second cooled syngas, wherein at least a portion of the steam is used to power a steam-driven compressor.

3. The process of claim 2, wherein at least a portion of the first cooled syngas and/or at least a portion of the second cooled syngas are introduced to the steam-driven compressor to yield compressed syngas.

4. The process of claim 3 further comprising (i) introducing at least a portion of the compressed syngas to a methanol reactor to produce a methanol reactor effluent stream; wherein the methanol reactor effluent stream comprises methanol, water, hydrogen, carbon monoxide, carbon dioxide, and hydrocarbons; and (ii) separating at least a portion of the methanol reactor effluent stream into a crude methanol stream and a vapor stream; wherein the crude methanol stream comprises methanol and water; and wherein the vapor stream comprises hydrogen, carbon monoxide, carbon dioxide, and hydrocarbons.

5. The process of claim 4, wherein a first portion of the vapor stream is recycled to the methanol reactor; and wherein a second portion of the vapor stream is purged and/or used as fuel.

6. The process of claim 4, wherein the methanol reactor is characterized by a methanol reactor volume that is decreased when compared to the volume of a methanol reactor used in an otherwise similar process that produces methanol from syngas generated via an SMR reactor without a CPO reactor; wherein the syngas generated via an SMR reactor without a CPO reactor is characterized by a $H_2$/CO molar ratio that is greater than the $H_2$/CO molar ratio of the syngas in step (c).

7. The process of claim 1, wherein the hydrocarbons comprise methane, natural gas, natural gas liquids, associated gas, well head gas, enriched gas, paraffins, shale gas, shale liquids, fluid catalytic cracking (FCC) off gas, refinery process gases, stack gases, fuel gas from a fuel gas header, or combinations thereof.

8. The process of claim 7:
   wherein the hydrocarbons further comprise one or more sulfur-containing compounds, and: wherein the process further comprises removing at least a portion of the sulfur-containing compounds from the heated first portion of hydrocarbons to yield a desulfurized first portion of hydrocarbons, and wherein the desulfurized first portion of hydrocarbons is fed to the CPO reactor in step (a); and/or
   wherein the process further comprises removing at least a portion of the sulfur-containing compounds from the heated second portion of hydrocarbons to yield a desulfurized second portion of hydrocarbons, and wherein the desulfurized second portion of hydrocarbons is fed to the SMR reactor in step (b).

9. The process of claim 8, wherein the process comprises removing the at least a portion of the sulfur-containing compounds from the heated first portion of hydrocarbons to yield the desulfurized first portion of hydrocarbons, and wherein the desulfurized first portion of hydrocarbons is fed to the CPO reactor in step (a), and wherein the process further comprises cooling the desulfurized first portion of hydrocarbons.

10. The process of claim 9:
    wherein cooling the desulfurized first portion of hydrocarbons comprises heating water while cooling the desulfurized first portion of hydrocarbons by heat exchange in a second heat exchanger to yield steam and a cooled desulfurized first portion of hydrocarbons, and wherein at least a portion of the cooled desulfurized first portion of hydrocarbons is fed to the CPO reactor in step (a); and wherein at least a portion of the steam produced by the second heat exchanger is optionally fed to the CPO reactor in step (a) and/or the SMR reactor in step (b).

11. The process of claim 1 further comprising (1) heating a feedstream comprising hydrocarbons to yield heated hydrocarbons; (2) optionally removing one or more sulfur-containing compounds from the heated hydrocarbons when present; and (3) splitting the heated hydrocarbons into the first portion of hydrocarbons and the second portion of hydrocarbons.

12. The process of claim 1, wherein a weight ratio of the first portion of hydrocarbons to the second portion of hydrocarbons is from about 1:9 to about 9:1.

13. The process of claim 1, wherein the CPO reactor is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 1.4:1 to about 5:1, wherein the C/O molar ratio refers to the total moles of carbon (C) of hydrocarbons in the reactant mixture divided by the total moles of oxygen (O2) in the reactant mixture; a steam to carbon (S/C) molar ratio in the CPO reactant mixture of from about 0 to about 2:1, wherein the S/C molar ratio refers to the total moles of water (H2O) in the reactant mixture divided by the total moles of carbon (C) of hydrocarbons in the reactant mixture; and combinations thereof.

14. The process of claim 1, wherein (1) the M ratio of the syngas is greater than or equal to about 1.7; (2) the H2/CO molar ratio of the syngas is greater than or equal to about 1.8; and/or (3) the SMR reactor is characterized by an S/C molar ratio in the SMR reactant mixture of greater than or equal to about 1.5:1.

15. A process for producing methanol comprising:
(a) heating a feedstream comprising hydrocarbons to yield heated hydrocarbons;
(b) optionally removing one or more sulfur-containing compounds from the heated hydrocarbons when present;
(c) splitting the heated hydrocarbons into a first portion of hydrocarbons and a second portion of hydrocarbons;
(d) feeding a catalytic partial oxidation (CPO) reactant mixture to a CPO reactor; wherein the CPO reactant mixture comprises oxygen, the first portion of hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen (H2), carbon monoxide (CO), carbon dioxide (CO2), water, and unreacted hydrocarbons, wherein the CPO reactor effluent is characterized by a hydrogen to carbon monoxide (H2/CO) molar ratio of the CPO reactor effluent, and wherein the CPO reactor effluent is characterized by an M ratio of the CPO reactor effluent, wherein the M ratio is a molar ratio defined as (H2-CO2)/(CO+CO2);
(e) feeding a steam methane reforming (SMR) reactant mixture to an SMR reactor, wherein the SMR reactant mixture comprises steam and the second portion of hydrocarbons; wherein at least a portion of the SMR reactant mixture reacts, via an SMR reaction, in the SMR reactor to produce an SMR reactor effluent; wherein the SMR reactor effluent comprises hydrogen (H2), carbon monoxide (CO), carbon dioxide (CO2), water, and unreacted hydrocarbons; wherein the SMR reactor effluent is characterized by a H2/CO molar ratio of the SMR reactor effluent that is greater than the H2/CO molar ratio of the CPO reactor effluent; wherein the SMR reactor effluent is characterized by an M ratio of the SMR reactor effluent that is greater than the M ratio of the CPO reactor effluent; and wherein a weight ratio of the first portion of hydrocarbons to the second portion of hydrocarbons is from about 1:4 to about 3:1;
(f) contacting at least a portion of the CPO reactor effluent with at least a portion of the SMR reactor effluent to yield syngas;
(g) heating water while cooling the syngas by heat exchange in a heat exchanger to yield steam and a cooled syngas;
(h) powering a steam-driven compressor with at least a portion of the steam;
(i) compressing at least a portion of the cooled syngas in the steam-driven compressor to yield compressed syngas;
(j) introducing at least a portion of the compressed syngas to a methanol reactor to produce a methanol reactor effluent stream; wherein the methanol reactor effluent stream comprises methanol, water, hydrogen, carbon monoxide, carbon dioxide, and hydrocarbons;
(k) separating at least a portion of the methanol reactor effluent stream into a crude methanol stream and a vapor stream; wherein the crude methanol stream comprises methanol and water; and wherein the vapor stream comprises hydrogen, carbon monoxide, carbon dioxide, and hydrocarbons; and
(l) recycling from about 90 wt. % to about 99 wt. % of the vapor stream, based on the total weight of the vapor stream to the methanol reactor.

16. The process of claim 15 further comprising (1) withdrawing a third portion of hydrocarbons from the feedstream prior to step (a), wherein the third portion of hydrocarbons is from about 5 wt. % to about 15 wt. % of the total hydrocarbons of the feedstream, based on the total weight of the total hydrocarbons, and wherein the total hydrocarbons are given by the sum of the first portion of hydrocarbons, the second portion of hydrocarbons, and the third portion of hydrocarbons; and (2) combusting the third portion of hydrocarbons to generate heat for heating the SMR reactor and/or generating additional steam, and wherein at least a portion of the additional steam is used to power the steam-driven compressor.

17. A system comprising:
(a) a catalytic partial oxidation (CPO) reactor operable to convert at least a portion of a CPO reactant mixture comprising oxygen, a first portion of hydrocarbons, and optionally steam, via a CPO reaction, to a CPO reactor effluent comprising hydrogen (¾), carbon monoxide (CO), carbon dioxide (CO2), water, and unreacted hydrocarbons, wherein the CPO reactor effluent is characterized by a hydrogen to carbon monoxide (H2/CO) molar ratio and an M ratio, wherein the M ratio is a molar ratio defined as (I I—CO)/(CO I CO2);
(b) a steam methane reforming (SMR) reactor operable to convert at least a portion of an SMR reactant mixture comprising steam and a second portion of hydrocarbons, via an SMR reaction, to an SMR reactor effluent comprising hydrogen (H2), carbon monoxide (CO), carbon dioxide (CO2), water, and unreacted hydrocarbons; wherein the SMR reactor effluent is characterized by a H2/CO molar ratio that is greater than the Tf/CO molar ratio of the CPO reactor effluent, and an M ratio that is greater than the M ratio of the CPO reactor effluent;

(c) one or more flow lines configured to combine at least a portion of the CPO reactor effluent with at least a portion of the SMR reactor effluent to provide a combined syngas stream upstream or downstream of a heat exchanger; and (d) the heat exchanger operable to transfer heat from at least a portion of the CPO reactor effluent, at least a portion of the SMR reactor effluent, or the combined syngas stream to the first portion of hydrocarbons, the second portion of hydrocarbons, or a combined hydrocarbon stream comprising the first portion of hydrocarbons and the second portion of hydrocarbons to yield a heated first portion of hydrocarbons, a heated second portion of hydrocarbons, or a heated combined hydrocarbon stream, respectively, wherein the combined syngas stream is characterized by an M ratio of greater than or equal to about 1.7 and/or an H2/CO molar ratio of greater than or equal to about 1.8.

18. The system of claim 17 further comprising a methanol synthesis reactor operable to produce a methanol reactor effluent stream comprising methanol from at least a portion of the combined syngas stream.

19. The system of claim 18 further comprising another heat exchanger downstream of the heat exchanger and operable to produce steam via heat exchange with the combined syngas stream.

20. The system of claim 19 further comprising a steam-driven compressor upstream of the methanol synthesis reactor and operable to compress the at least a portion of the combined syngas stream, wherein at least a portion of the steam for powering a turbine of the steam-driven compressor comprises the steam produced via heat exchange with the combined syngas stream.

* * * * *